US012049672B2

(12) United States Patent
Qi et al.

(10) Patent No.: US 12,049,672 B2
(45) Date of Patent: Jul. 30, 2024

(54) METHODS AND SYSTEMS FOR SCREENING FOR CONDITIONS

(71) Applicant: GRAIL, LLC, Menlo Park, CA (US)

(72) Inventors: Rongsu Qi, Mountain View, CA (US); Farooq A. Siddiqui, San Jose, CA (US); Srinka Ghosh, San Francisco, CA (US)

(73) Assignee: GRAIL, LLC, Menlo Park, CA (US)

( * ) Notice: Subject to any disclaimer, the term of this patent is extended or adjusted under 35 U.S.C. 154(b) by 79 days.

(21) Appl. No.: 17/018,692

(22) Filed: Sep. 11, 2020

(65) Prior Publication Data

US 2021/0087637 A1 Mar. 25, 2021

Related U.S. Application Data

(63) Continuation of application No. PCT/US2019/028804, filed on Apr. 23, 2019.

(60) Provisional application No. 62/661,529, filed on Apr. 23, 2018.

(51) Int. Cl.
*C12Q 1/6886* (2018.01)
*C12Q 1/6827* (2018.01)

(52) U.S. Cl.
CPC ......... *C12Q 1/6886* (2013.01); *C12Q 1/6827* (2013.01); *C12Q 2600/112* (2013.01)

(58) Field of Classification Search
CPC .... G16B 20/10; C12Q 1/6869; C12Q 1/6827; C12Q 1/6886
See application file for complete search history.

(56) References Cited

U.S. PATENT DOCUMENTS

| | | | |
|---|---|---|---|
| 2010/0112590 A1 | 5/2010 | Lo et al. | |
| 2013/0034546 A1 | 2/2013 | Rava et al. | |
| 2013/0178389 A1 | 7/2013 | Lapidus et al. | |
| 2016/0340740 A1 | 11/2016 | Zhang | |
| 2017/0121767 A1 | 5/2017 | Dor et al. | |
| 2017/0329893 A1 | 11/2017 | Di Iulio et al. | |

FOREIGN PATENT DOCUMENTS

| | | | | |
|---|---|---|---|---|
| WO | WO-2008038000 A1 | 4/2008 | | |
| WO | WO-2012149042 A2 | 11/2012 | | |
| WO | WO-2013132305 A1 | 9/2013 | | |
| WO | WO-2014043763 A1 | 3/2014 | | |
| WO | WO-2015184404 A1 * | 12/2015 | ........... | C12Q 1/6858 |
| WO | WO-2016008451 A1 | 1/2016 | | |
| WO | WO-2016015058 A2 | 1/2016 | | |
| WO | WO-2018057770 A1 | 3/2018 | | |
| WO | WO-2018081130 A1 | 5/2018 | | |
| WO | WO-2019209884 A1 | 10/2019 | | |

OTHER PUBLICATIONS

Howell et al. Hepat Oncol. 2016. 3(1):45-55. (Year: 2016).*
Berrieman et al. Chromosomal analysis of non-small-cell lung cancer by multicolour fluorescent in situ hybridisation. Brit J Cancer 2004;90:900-905.
Chen, Ming-Luan, et al. Quantification of 5-Methylcytosine and 5-Hydroxymethylcytosine in Genomic DNA from Hepatocellular Carcinoma Tissues by Capillary Hydrophilic-Interaction Liquid Chromatography/Quadrupole TOF Mass Spectometry, Clinical Chemistry, 2013, vol. 59, No. 5, pp. 824-832.
Diehl, et al. Detection and quantification of mutations in the plasma of patients with colorectal tumors. Proc Natl Acad Sci U S A. Nov. 8, 2005;102(45):16368-73. Epub Oct. 28, 2005.
Kusano et al. Chromosomal imbalances detected by comparative genomic hybridization are associated with outcome of patients with hepatocellular carcinoma. Cancer 2002; 94:746-751.
Laurent-Puig et al. Genetic alterations associated with hepatocellular carcinomas define distinct pathways of hepatocarcinogenesis. Gastroenterology 2001; 120:1763-1773.
Lian, Christine Guo, et al. Loss of 5-Hydroxymethylcytosine as an Epigenetic Hallmark of Melanoma, Cell, Sep. 14, 2012, vol. 150, No. 6, pp. 1135-1146.
Yan, Linlin, "Diagnostic value of circulating cell-free DNA levels for hepatocellular carcinoma", International Journal of Infectious Diseases, vol. 67, 92-97, 2018.
Luk et al. Molecular cytogenetic analysis of non-small cell lung carcinoma by spectral karyotyping and comparative genomic hybridization. Cancer Genet Cytogen 2001;125:87-99.
Moinzadeh et al. Chromosome alterations in human hepatocellular carcinomas correlate with aetiology and histological grade—results of an explorative CGH meta-analysis. Brit J Cancer 2005;92:935-941.
Nakao et al. High-resolution analysis of DNA copy number alterations in colorectal cancer by array-based comparative genomic hybridization. Carcinogenesis 2004;25:1345-1357.
Nishizaki et al. Genetic alterations in lobular breast cancer by comparative genomic hybridization.Int J Cancer 1997; 74:513-517.
Olshen, et al. Circular binary segmentation for the analysis of array-based DNA copy number data. Biostatistics. Oct. 2004;5(4):557-72.
O'Marcaigh, Aengus S. et al. Estimating the Predictive Value of a Diagnostic Test, Clinical Pediatrics, 32(8):485-491 (Aug. 1, 1993).
PCT/US19/28804 International Search Report & Written Opinion dated Aug. 30, 2019.
Pei et al. Genomic imbalances in human lung adenocarcinomas and squamous cell carcinomas. Gene Chromosome Canc 2001;31:282-287.
Persson et al. Chromosomal aberrations in breast cancer: A comparison between cytogenetics and comparative genomic hybridization. Gene Chromosome Canc 1999; 25: 115-122.
Peterson et al. Patterns of Chromosomal Imbalances in Adenocarcinoma and Squamous Cell Carcinoma of the Lung. Cancer Res 1997; 57:2331-2335.

(Continued)

*Primary Examiner* — Joseph G. Dauner

(74) *Attorney, Agent, or Firm* — Sheppard Mullin Richter & Hampton LLP

(57) ABSTRACT

Methods are provided to improve the positive predictive value for cancer detection using cell-free nucleic acid samples. The methods can include the use of at least two assays. The assays can vary, for example, with respect to sensitivity, specificity, sequencing depth, analyte, and cost. An exemplary method can be used to provide an initial cancer assay with high sensitivity and a follow-up assay with high specificity in detecting cancer.

14 Claims, 6 Drawing Sheets

(56) References Cited

OTHER PUBLICATIONS

Pinkel, et al. High resolution analysis of DNA copy number variation using comparative genomic hybridization to microarrays. Nat Genet. Oct. 1998;20(2):207-11.
Richard et al. Patterns of chromosomal imbalances in invasive breast cancer. Int J Cancer 2000; 89: 305-310.
Schraml et al. Combined Array Comparative Genomic Hybridization and Tissue Microarray Analysis Suggest PAK1 at 11q13.5-q14 as a Critical Oncogene Target in Ovarian Carcinoma. Am J Pathol 2003; 163:985-992.
Sonoda et al. Comparative genomic hybridization detects frequent overrepresentation of chromosomal material from 3q26, 8q24, and 20q13 in human ovarian carcinomas. Gene Chromosome Canc 1997; 20:320-328.
Taetle et al. Chromosome abnormalities in ovarian adenocarcinoma: I. nonrandom chromosome abnormalities from 244 cases. Gene Chromosome Canc 1999; 25: 290-300.
Tirkkonen et al. Molecular cytogenetics of primary breast cancer by CGH. Gene Chromosome Canc 1998; 21: 177-184.
Tsafrir, et al. Relationship of gene expression and chromosomal abnormalities in colorectal cancer. Cancer Res. Feb. 15, 2006;66(4):2129-37.

\* cited by examiner

METHODS AND SYSTEMS FOR SCREENING FOR CONDITIONS

CROSS-REFERENCE

This application is a continuation of International Patent Application No. PCT/US2019/028804, filed on Apr. 23, 2019, which claims the benefit of U.S. Provisional Application No. 62/661,529 filed on Apr. 23, 2018, each of which is incorporated herein by reference in its entirety.

BACKGROUND

Tumors can deposit fragmented DNA into the bloodstream, which has sparked interest in the development of so-called "liquid biopsies." These non-invasive methods seek to determine the presence, location, and/or type of tumor in a subject using cell-free samples, such as plasma. Many tumors can be treatable if detected early in their development. However, current methods can lack the sensitivity and/or specificity to detect a tumor at an early stage and can return a large number of false positive or false negative results. The sensitivity of a test can refer to the likelihood that a subject that is positive for a condition tests positive for the condition. The specificity of a test can refer to the likelihood that a subject that is negative for a condition tests negative for that condition. The problems of sensitivity and specificity can be exaggerated in assays for the early detection of tumors, for example, because samples on which such tumor detection methods are performed can have relatively small amounts of tumor-derived DNA and because the condition itself can have a relatively low prevalence among individuals tested in the early stage. Accordingly, there is a clinical need for methods having higher sensitivity and/or specificity for the detection of tumors.

Provided herein are methods that utilize combinations of assays to improve the positive predictive value of the tests over the use of single assays alone.

SUMMARY

Described herein, in certain embodiments, are methods of screening for a condition of a subject, the method comprising: performing a first assay comprising: obtaining a first plurality of sequencing reads at a first read depth from a first sample comprising cell-free nucleic acids obtained from the subject, analyzing the first plurality of sequencing reads for a copy number aberration; and detecting a presence of the copy number aberration in the first plurality of sequencing reads; conditionally performing a second assay upon the detection of the copy number aberration in the first plurality of sequencing reads, the second assay comprising: obtaining a second plurality of sequencing reads at a second read depth from a second sample comprising cell-free nucleic acids obtained from the subject; analyzing the second plurality of sequencing reads for a biomarker of the condition of the subject, thereby screening the subject for the condition based on detecting the biomarker in the second plurality of sequencing reads, wherein the second plurality of sequencing reads comprises a greater read depth than the first plurality of sequencing reads and wherein a positive predictive value of screening the subject for the condition based on the second assay is greater than a positive predictive value of screening the subject for the condition based on the first assay alone.

In some embodiments, the first plurality of sequencing reads comprises sequencing reads from a whole genome survey. In some embodiments, the first plurality of sequencing reads comprises sequencing reads informative of a methylation profile of the cell-free nucleic acids in the first sample. In some embodiments, the read depth of the first plurality of sequencing reads is 10× or less, 5× or less, 4× or less, 3× or less, or 2× or less. In some embodiments, the read depth of the second plurality of sequencing reads is 5× or less, 10× or less, 20× or less, 50× or less, 100× or less, 250× or less, 500× or less, 1,000× or less, 2,500× or less, 5,000× or less, 10,000× or less, 15,000× or less, 20,000× or less, 30,000× or less, 40,000× or less, 50,000× or less, 75,000× or less, 100,000× or less, or 250,000× or less. In some embodiments, the first plurality of sequencing reads comprises 200 million reads or less, 100 million reads or less, 80 million reads or less, 60 million reads or less, or 40 million reads or less. In some embodiments, the second plurality of sequencing reads comprises 100 million reads or more, 200 million reads or more, 400 million reads or more, 1 billion reads or more, 2 billion reads or more, 5 billion reads or more, 10 billion reads or more, 20 billion reads or more, or 50 billion reads or more.

In some embodiments, the second plurality of sequencing reads comprises sequencing reads from a whole genome survey. In some embodiments, the second plurality of sequencing reads comprises sequencing reads from a targeted region of a genome, wherein the targeted region of the genome comprises a subset of chromosomes, a single chromosome, a subset of genomic loci, or a single genomic locus. In some embodiments, detecting the presence of the copy number aberration in the first plurality of sequencing reads comprises comparing an amount of the first plurality of sequencing reads originating from a first chromosomal region to a cutoff value. In some embodiments, detecting the presence of the copy number aberration in the first plurality of sequencing reads comprises detecting an absolute number of sequencing reads identified as originating from the first chromosomal region.

In some embodiments, detecting the presence of the copy number aberration in the first plurality of sequencing reads comprises detecting the copy number aberration originating from a first tissue of interest. In some embodiments, the tissue of interest is a liver tissue, a lung tissue, a pancreatic tissue, a stomach tissue, a brain tissue, a cardiac tissue, a muscle, a kidney tissue, a red blood cell, or a skin tissue. In some embodiments, the biomarker of the condition comprises a presence of the copy number aberration in the second plurality of sequencing reads, and wherein the second assay comprises comparing an amount of the second plurality of sequencing reads originating from the first chromosomal region to a cutoff value. In some embodiments, detecting the presence of the copy number aberration in the second plurality of sequencing reads comprises comparing an amount of the second plurality of sequencing reads originating from a second chromosomal region to a cutoff value. In some embodiments, detecting the presence of the copy number aberration in the second plurality of sequencing reads comprises detecting an absolute number of sequencing reads identified as originating from the first chromosomal region. In some embodiments, detecting the presence of the copy number aberration in the second plurality of sequencing reads comprises detecting an absolute number of sequencing reads identified as originating from the second chromosomal region. In some embodiments, detecting the presence of the copy number aberration in the second plurality of sequencing reads comprises detecting a copy number aberration originating from the first tissue of interest. In some embodiments, detecting the presence of the copy number aberration in the second plurality of sequencing reads comprises detecting a copy number aberration originating from a second tissue of interest.

In some embodiments, the second tissue of interest is a liver tissue. In some embodiments, the first tissue of interest and the second tissue of interest are the same. In some embodiments, the method further comprises obtaining the first sample comprising cell-free nucleic acids from the subject. In some embodiments, the method further comprises sequencing the cell-free nucleic acids in the first sample to obtain the first plurality of sequencing reads at the first read depth. In some embodiments, the method further comprises obtaining the second sample comprising cell-free nucleic acids from the subject. In some embodiments, the method further comprises sequencing the cell-free nucleic acids in the second sample to obtain the second plurality of sequencing reads at the second read depth.

In some embodiments, the first sample and the second sample are obtained from the subject at the same time. In some embodiments, the first sample and the second sample are each a subsample of a single blood draw from the subject. In some embodiments, the second assay is performed within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after performing the first assay. In some embodiments, the second sample is cryogenically preserved for 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after performing the first assay. In some embodiments, the condition is a liver condition. In some embodiments, the liver condition is selected from the group consisting of liver cirrhosis, hepatocellular carcinoma, nonalcoholic fatty liver disease, nonalcoholic steatohepatitis, and a combination thereof. In some embodiments, the at least a subset of the first plurality of cell-free nucleic acids and the at least a subset of the second plurality of cell-free nucleic acids comprise cell-free nucleic acids that are from a hepatocellular carcinoma. In some embodiments, the copy number aberration comprises a duplication or a deletion of a genomic locus. In some embodiments, the second assay comprises determining that a subset of the second plurality of cell-free nucleic acids is from a liver tissue. In some embodiments, the condition is a cancer type, and wherein the second assay is used to determine the cancer type. In some embodiments, the cancer type is hepatocellular carcinoma.

In some embodiments, the first plurality of cell-free nucleic acids and the second plurality of cell-free nucleic acids are from one or more plasma samples. In some embodiments, the first plurality of cell-free nucleic acids comprises deoxyribonucleic acids. In some embodiments, the first plurality of cell-free nucleic acids comprises ribonucleic acids. In some embodiments, the second plurality of cell-free nucleic acids comprises deoxyribonucleic acids. In some embodiments, the second plurality of cell-free nucleic acids comprises ribonucleic acids. In some embodiments, the first assay comprises an amplification of the first plurality of cell-free nucleic acids before the sequencing. In some embodiments, the amplification comprises a whole genome amplification or a targeted amplification. In some embodiments, the first plurality of cell-free nucleic acids are not amplified before the sequencing. In some embodiments, the first plurality of cell-free nucleic acids are analyzed for the copy number aberration based on re-binning, combining windows, or hidden Markov model analysis, or a combination thereof.

In some embodiments, performing the second assay comprises determining a methylation status of the second sample of cell-free nucleic acids. In some embodiments, the methylation status of a subset of the cell-free nucleic acids from the second sample is used to identify a tissue of origin of the subset of the cell-free nucleic acids from the second sample. In some embodiments, the tissue of origin is a liver tissue. In some embodiments, the methylation status of a subset of the cell-free nucleic acids from the second sample is used to identify a cancer type from which the subset is derived. In some embodiments, the cancer type is hepatocellular carcinoma. In some embodiments, determining the methylation status comprises determining a methylation haplotype.

In some embodiments, the second assay comprises analyzing a fragment size of a subset of cell free nucleic acids from the second sample. In some embodiments, the method further comprises using the fragment size to identify a tissue from which the subset of the cell-free nucleic acids from the second sample is derived. In some embodiments, the tissue is a liver tissue. In some embodiments, the method further comprises using the fragment size to identify a cancer type from which the subset of the cell-free nucleic acids from the second sample is derived. In some embodiments, the cancer type is hepatocellular carcinoma. In some embodiments, the analyzing the fragment size comprises filtering out sequences above a size threshold.

In some embodiments, the second assay comprises identifying somatic mutations in the second sample comprising cell-free nucleic acids. In some embodiments, the second assay comprises filtering out sequence reads corresponding to somatic mutations in white blood cells from the subject. In some embodiments, the positive predictive value for the condition being present based on the second assay is at least 1.5-fold, 2-fold, 5-fold, 10-fold, 20-fold, 50-fold, or 100-fold greater than the positive predictive value for the condition being present based on the first assay. In some embodiments, the positive predictive value for the condition being present based on the first assay and the second assay is at least 1.5-fold, 2-fold, 5-fold, 10-fold, 20-fold, 50-fold, or 100-fold greater than the positive predictive value for the condition being present based on the first assay.

Further described herein, in certain embodiments, are methods of screening for a condition of a subject, the method comprising: (a) obtaining a first plurality of cell-free nucleic acids from the subject, wherein at least a subset of the first plurality of cell-free nucleic acids is potentially originated from a liver tissue of the subject; (b) performing a first assay comprising analyzing sequencing data of the first plurality of cell-free nucleic acids for copy number aberrations; (c) performing a second assay comprising analyzing sequencing data of a second plurality of cell-free nucleic acids from the subject, wherein at least a subset of the second plurality of cell-free nucleic acids is potentially originated from a liver tissue of the subject, wherein a positive predictive value for the condition being present based on the first assay and the second assay is greater than a positive predictive value for the condition being present based on the first assay, thereby screening for the condition of the subject. In some embodiments, the condition is a liver condition. In some embodiments, the liver condition is selected from the group consisting of liver cirrhosis, hepatocellular carcinoma, nonalcoholic fatty liver disease, nonalcoholic steatohepatitis, and a combination thereof.

In some embodiments, the first plurality of cell-free nucleic acids and the second plurality of cell free nucleic acids are from one or more biological samples from the subject. In some embodiments, the first plurality of cell-free nucleic acids and the second plurality of cell free nucleic acids are the same. In some embodiments, the at least a subset of the first plurality of cell-free nucleic acids and the at least a subset of the second plurality of cell-free nucleic acids comprise cell-free nucleic acids that are from hepatocellular carcinoma. In some embodiments, the copy number aberration comprises a duplication or a deletion of a genomic locus. In some embodiments, the second assay is used to determine that the subset of the second plurality of cell-free nucleic acids is from the liver tissue. In some embodiments, the condition is a cancer type, and wherein the second assay is used to determine the cancer type. In some embodiments, the cancer type is hepatocellular carcinoma.

In some embodiments, the first plurality of cell-free nucleic acids and the second plurality of cell-free nucleic acids are from one or more plasma samples. In some embodiments, the first plurality of cell-free nucleic acids comprises deoxyribonucleic acids or ribonucleic acids. In some embodiments, the second plurality of cell-free nucleic acids comprises deoxyribonucleic acids or ribonucleic acids. In some embodiments, the sequencing comprises whole genome sequencing or targeted sequencing. In some embodiments, the first assay comprises an amplification of the first plurality of cell-free nucleic acids before the sequencing. In some embodiments, the amplification comprises a whole genome amplification or a targeted amplification. In some embodiments, the first plurality of cell-free nucleic acids are not amplified before the sequencing. In some embodiments, the first plurality of cell-free nucleic acids are analyzed for the copy number aberration based on re-binning, combining windows, or hidden Markov model analysis.

In some embodiments, an average fragment size of the at least a subset of the first plurality of cell-free nucleic acids is smaller than an average fragment size of the other cell-free nucleic acids from the first plurality of cell-free nucleic acids. In some embodiments, an average fragment size of the at least a subset of the second plurality of cell-free nucleic acids is smaller than an average fragment size of the other cell-free nucleic acids from the second plurality of cell-free nucleic acids.

In some embodiments, the second assay comprises determining a methylation status of the second plurality of cell-free nucleic acids. In some embodiments, the methylation status of a subset of the cell-free nucleic acids from the second biological sample is used to identify a tissue origin of the cell-free nucleic acids from the second biological sample. In some embodiments, the tissue origin is liver. In some embodiments, the methylation status of a subset of the cell-free nucleic acids from the second biological sample is used to identify a cancer type from which the subset is derived. In some embodiments, the cancer type is hepatocellular carcinoma. In some embodiments, the methylation status comprises a methylation haplotype.

In some embodiments, the second assay comprises analyzing a fragment size of the second plurality of cell-free nucleic acids. In some embodiments, the fragment size to identify a tissue from which the subset of the plurality of cell-free nucleic acids is derived. In some embodiments, the tissue is a liver tissue. In some embodiments, the method further comprises using the fragment size to identify a cancer type from which the subset of the plurality of cell-free nucleic acids is derived. In some embodiments, the cancer type is hepatocellular carcinoma. In some embodiments, the analyzing the fragment size comprises filtering out sequences above a size threshold.

In some embodiments, the positive predictive value for the condition being present based on the first assay and the second assay is at least 1.5-fold, 2-fold, 5-fold, 10-fold, 20-fold, 50-fold, or 100-fold greater than the positive predictive value for the condition being present based on the first assay. In some embodiments, the second assay comprises identifying a somatic mutation in the second plurality of cell-free nucleic acids. In some embodiments, the second assay comprises filtering out sequence reads corresponding to the somatic mutation in white blood cells from the subject. In some embodiments, the first assay comprises analyzing sequence reads from a reference chromosome. In some embodiments, the first assay comprising analyzing sequence reads at a first depth of 10× or less, 5× or less, 4× or less, 3× or less, or 2× or less. In some embodiments, the second assay comprises analyzing sequence reads at a second depth, wherein the second depth is greater than the first depth. In some embodiments, the second depth is greater than 5×, greater than 10×, greater than 10,000×, or greater than 30,000×. In some embodiments, the first assay is performed before the second assay.

Further disclosed herein, in certain embodiments, are methods of determining a copy number variation for a subject having or suspected of having a condition, the method comprising: (a) obtaining a first plurality of cell-free nucleic acids from the subject; (b) performing a first assay comprising obtaining sequencing data of the first plurality of cell-free nucleic acids at a first read depth to determine a first assay copy number; (c) comparing the first assay copy number to a threshold to indicate the presence of the copy number variation; (d) obtaining a second plurality of cell-free nucleic acids from the subject; (e) performing a second assay comprising obtaining sequencing data of the second plurality of cell-free nucleic acids from the subject at a second read depth greater than the first read depth to determine a second assay copy number; (f) comparing the second assay copy number to the threshold to indicate the presence of the copy number variation, wherein a positive predictive value for the copy number variation being present based on the first assay and the second assay is greater than a positive predictive value for the copy number variation being present based on the first assay. In some embodiments, the copy number variation is a copy number gain or a copy number loss relative to a subject not having the condition.

In some embodiments, the first read depth is less than 10×. In some embodiments, the first read depth is selected from the group consisting of: 1×, 1.5×, 2×, 2.5×, 3×, 3.5×, 4×, 4.5×, and 5×. In some embodiments, the second read depth is greater than 10×. In some embodiments, the threshold is a copy number determined from a plurality of individuals who do not suffer from the condition. In some embodiments, the subject comprises the copy number variation when the first assay copy number is above the threshold. In some embodiments, the subject comprises the copy number variation when the second assay copy number is above the threshold. In some embodiments, the threshold is a distance from the baseline copy number. In some embodiments, the second plurality of cell-free nucleic acids comprises cell-free nucleic acids from a targeted region of the genome of the subject. In some embodiments, the targeted region is a region associated with the condition. In some embodiments, the targeted region is a region identified in the first assay as having the copy number variation.

Further described herein, in certain embodiments, are methods of screening for a hepatocellular carcinoma in a subject, the method comprising: (a) obtaining a first plurality of cell-free nucleic acids from the subject, wherein at least a subset of the first plurality of cell-free nucleic acids is potentially originated from a liver tissue; (b) performing a first assay to analyze the first plurality of cell-free nucleic acids for a copy number aberration, the first assay comprising sequencing the first plurality of cell-free nucleic acids; (c) performing a second assay, the second assay comprising determining a methylation status of a second plurality of cell-free nucleic acids from the subject, wherein at least a subset of the second plurality of cell-free nucleic acids is potentially originated from the liver tissue; and (d) comparing the methylation status with one or more reference methylation statuses associated with a hepatocellular carcinoma, thereby screening for the hepatocellular carcinoma in the subject.

Further described herein, in certain embodiments, are methods of screening for a hepatocellular carcinoma in a subject, the method comprising: (a) obtaining a first plurality of cell-free nucleic acids from the subject, wherein at least a subset of the first plurality of cell-free nucleic acids is potentially from a liver tissue; (b) performing a first assay to analyze the first plurality of cell-free nucleic acids for a copy number aberration, the first assay comprising sequencing the first plurality of cell-free nucleic acids; (c) performing a second assay to analyze a fragment size of a second plurality of cell-free nucleic acids from the subject, wherein at least a subset of the second plurality of cell-free nucleic acids is potentially from a liver cancer; and (d) comparing the fragment size with one or more reference fragment sizes associated with the hepatocellular carcinoma thereby screening for the hepatocellular carcinoma in the subject.

Further described herein, in certain embodiments, are non-transitory computer-readable mediums comprising instructions operable, when executed by one or more computer processors of a computer system, to cause the computer system to: obtaining a first plurality of sequencing reads at a first read depth from a first sample comprising cell-free nucleic acids obtained from the subject, analyze a first plurality of sequencing reads obtained at a first read depth from a first sample comprising cell-free nucleic acids obtained from a subject for a copy number aberration; and detect a presence of the copy number aberration in the first plurality of sequencing reads; conditionally analyze a second plurality of sequencing reads at a second read depth from a second sample comprising cell-free nucleic acids obtained from the subject for a biomarker of a condition of the subject, thereby screening the subject for the condition based on detecting the biomarker in the second plurality of sequencing reads, wherein analyzing the second plurality of sequencing reads is conditionally performed upon the detection of the copy number aberration in the first plurality of sequencing reads; wherein the second plurality of sequencing reads comprises a greater read depth than the first plurality of sequencing reads; and wherein a positive predictive value of screening the subject for the condition based on the analyzing the second plurality of sequencing reads is greater than a positive predictive value of screening the subject for the condition based on analyzing the first plurality of sequencing reads alone.

Further described herein, in certain embodiments, are computer-implemented systems comprising: a digital processing device comprising: at least one processor, an operating system configured to perform executable instructions, a memory, and a computer program including instructions executable by the digital processing device to create an application comprising: a software module for obtaining a first plurality of sequencing reads at a first read depth from a first sample comprising cell-free nucleic acids obtained from the subject, analyzing a first plurality of sequencing reads obtained at a first read depth from a first sample comprising cell-free nucleic acids obtained from a subject for a copy number aberration; and detecting a presence of the copy number aberration in the first plurality of sequencing reads; and a software module for conditionally analyzing a second plurality of sequencing reads at a second read depth from a second sample comprising cell-free nucleic acids obtained from the subject for a biomarker of a condition of the subject, thereby screening the subject for the condition based on detecting the biomarker in the second plurality of sequencing reads, wherein analyzing the second plurality of sequencing reads is conditionally performed upon the detection of the copy number aberration in the first plurality of sequencing reads; wherein the second plurality of sequencing reads comprises a greater read depth than the first plurality of sequencing reads; and wherein a positive predictive value of screening the subject for the condition based on the analyzing the second plurality of sequencing reads is greater than a positive predictive value of screening the subject for the condition based on analyzing the first plurality of sequencing reads alone.

Further described herein, in certain embodiments, are non-transitory computer-readable mediums comprising instructions operable, when executed by one or more computer processors of a computer system, to cause the computer system to: (a) analyze sequencing reads received from sequencing a first plurality of cell-free nucleic acids from a subject for a copy number aberration, wherein at least a subset of the first plurality of cell-free nucleic acids is potentially from a liver tissue of the subject, wherein less than 60 million sequence reads are analyzed; and (b) analyze sequencing reads received from sequencing a second plurality of cell-free nucleic acids from the subject, wherein at least a subset of the second plurality of cell-free nucleic acids is potentially from the liver tissue of the subject; wherein a positive predictive value for a condition being present in the subject based on (a) and (b) is greater than a positive predictive value for the condition being present in the subject based on (a), thereby screening for the condition of the subject.

Further described herein, in certain embodiments, are non-transitory computer-readable mediums comprising instructions operable, when executed by one or more computer processors of a computer system, to cause the computer system to: (a) analyze sequencing reads received from sequencing a first plurality of cell-free nucleic acid from a subject for a copy number aberration, wherein at least a subset of the first plurality of cell-free nucleic acids is potentially from a liver tissue from the subject; and (b) analyze sequencing reads received from sequencing a second plurality of cell-free nucleic acids from the subject, the analysis comprising determining a methylation status of the second plurality of cell-free nucleic acids, wherein at least a subset of the second plurality of cell-free nucleic acids is potentially from the liver tissue from the subject; and (c) compare the methylation status with one or more reference methylation statuses associated with hepatocellular carcinoma, thereby screening for hepatocellular carcinoma in the subject.

Further described herein, in certain embodiments, are non-transitory computer-readable mediums comprising instructions operable, when executed by one or more computer processors of a computer system, to cause the computer system to: (a) analyze sequencing reads received from sequencing a first plurality of cell-free nucleic acids from a subject for a copy number aberration, wherein at least a subset of the first plurality of cell-free nucleic acids is potentially from a liver tissue from the subject; and (b) analyze sequencing reads received from sequencing a second plurality of cell-free nucleic acids from the subject, the analysis comprising determining a fragment size of the second plurality of cell-free nucleic acids, wherein at least a subset of the second plurality of cell-free nucleic acids is potentially from the liver tissue of the subject; and (c) compare the fragment size with one or more reference fragment sizes associated with hepatocellular carcinoma, thereby screening for hepatocellular carcinoma in the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
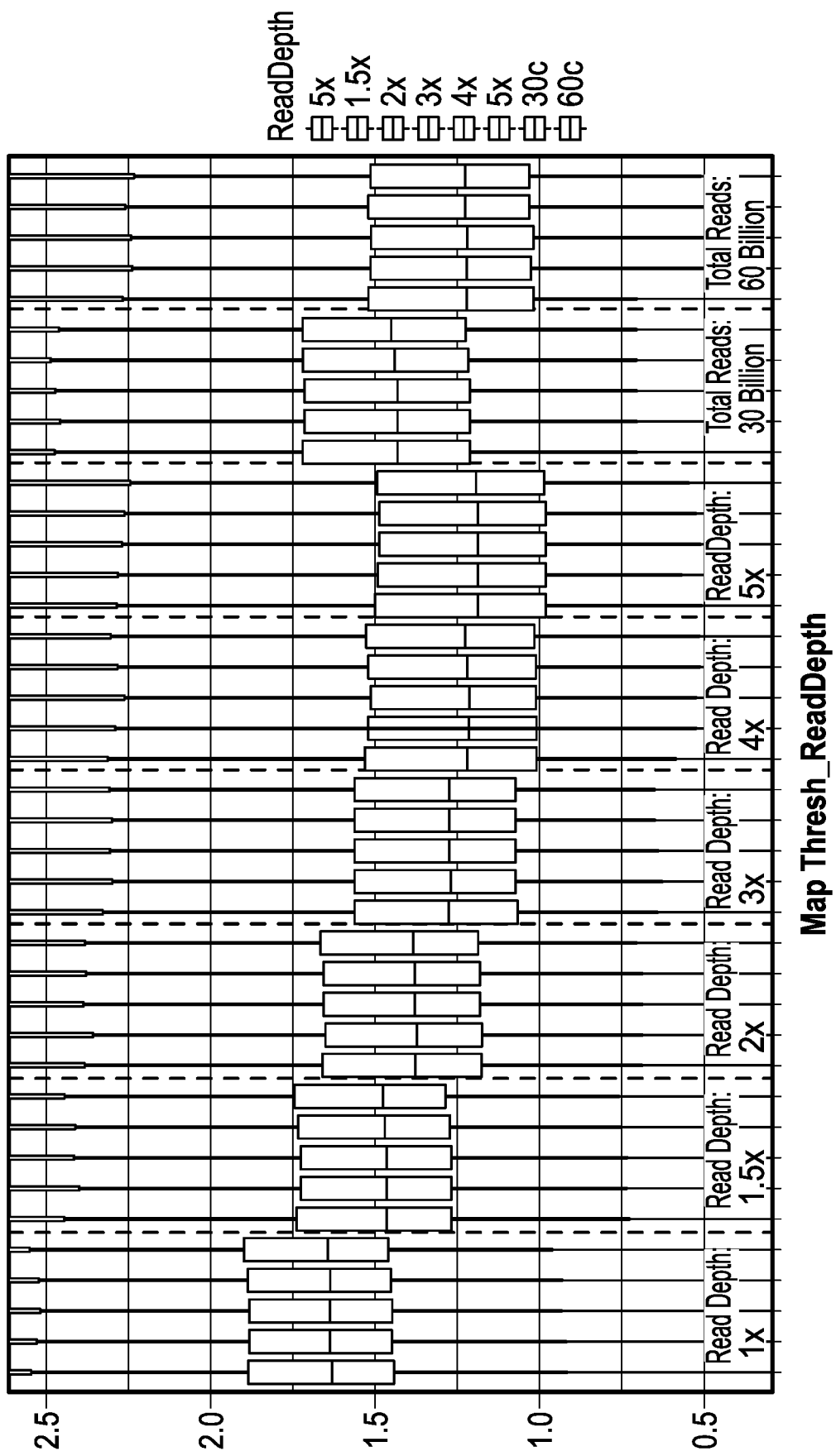
FIG. 1 illustrates percent Coefficient of Variance (CV) of sequencing data for 40 normal individuals for each 1 MB genomic data. The X axis shows mappability threshold based on the read depth. Results are shown in groups of five thresholds with the same read depth (groups from left to right are 1×, 1.5×, 2×, 3×, 4×, 5×, 30 billion reads, and 60 billion reads. Within each group, the X axis reads 0.5, 0.66, 0.76, 0.8, and 0.85. The Y axis shows % CV and reads 0.5, 1.0, 1.5, 2.0, and 2.5 from bottom to top.

Analysis of circulating, cell-free DNA can be a non-invasive and easily accessible way to assess a condition, make a diagnosis and/or prognosis, and provide guidance for treatment. However, subsets of cell-free DNA with a low concentration in the blood can be difficult to detect. A single, high sensitivity test can be useful for assessing a condition when its result is negative. A positive result, however, may not be ideal in providing a disease diagnosis or prognosis due to the potential for false positives. Similarly, a single, high specificity test can be useful for assessing a disease when its result is positive. An increase in the specificity of an assay, however, can result in an increase in false negatives. The present disclosure is directed to methods of using combinations of tests to increase the positive predictive value of detecting, diagnosing, prognosing, or assessing a disease or condition.

Provided herein are methods of detecting a disease or condition in a subject. The methods can involve the use of two or more assays. The assays can be performed to assess the presence or state of the condition in the subject. The second assay can be performed concurrently or sequentially with the first assay. If a first assay and a second assay are performed sequentially, the second assay can be conditionally performed in some embodiments if the result of the first assay indicates a likelihood that the disease or condition is present in the subject above a certain threshold. The combination of the results of the first assay and the second assay can have a higher positive predictive value than the results of the first assay alone. Increasing the positive predictive value via performance of both a first and second assay can help correctly identify or assess subjects who have a condition.

The present disclosure provides methods for increasing the positive predictive value or precision for screening a subject for a condition, such as cancer, and for reducing a false positive rate. The positive predictive value can correspond to a ratio of subjects who are actually positive for a condition (true positives) to subjects identified as having the condition (true positives+false positives). In particular, methods of the present disclosure can include performing a first assay with a high sensitivity and low positive predictive value, followed by a second, high specificity assay for those samples that are positive in the first assay, thereby increasing the positive predictive value of the overall screen. Increasing the positive predictive value for a cancer screen can help correctly identify subjects who have cancer, and can reduce the pool of subjects subjected to additional expensive and/or invasive assays.

Thus, the present disclosure provides methods for assessing a condition in a subject. Exemplary conditions include cancer and liver conditions, including liver cancers. In some cases, the liver cancer is hepatocellular carcinoma. Assessing a condition can comprise performing one or more assays to identify the presence of the condition. In particular, methods of the present disclosure can include performing a first assay to analyze a first biological sample and a second assay to analyze a second biological sample. In some cases, the biological samples can be the same biological sample. For example, the biological samples can be two or more aliquots of the same blood draw or plasma sample. In other cases, the biological samples can be different. For example, the biological samples can be two different plasma samples obtained at different times. Both a first and second assay can be performed on samples obtained using noninvasive methods, thereby minimizing the need for unnecessary invasive testing. Examples of noninvasive methods include the collection of blood, serum, or plasma.

In some cases, a biological sample can be obtained from a subject. The biological sample can comprise cell-free nucleic acid, which can be analyzed by one or more assays as disclosed herein. At least a subset of cell-free nucleic acid in a biological sample can be from liver tissue of a subject. Alternatively or in addition, at least a subset of cell-free nucleic acid in a biological sample can be from hepatocellular carcinoma.

In some embodiments, an assay can comprise nucleic acid sequencing, e.g., DNA sequencing. DNA sequencing can include high-throughput or next-generation sequencing. An assay can comprise analyzing cell-free nucleic acid from a biological sample for copy number aberrations. An assay can comprise determining a methylation status of cell-free nucleic acid from a biological sample. An assay can comprise analyzing a fragment size of cell-free nucleic acid from a biological sample. An assay can comprise analyzing an endpoint of cell-free nucleic acid from a biological sample. An assay can comprise detecting mutations present in cell-free nucleic acid from a biological sample. An assay can serve to identify a subset of cell-free nucleic acid as derived from liver tissue from a subject. An assay can serve to identify a subset of cell-free nucleic acid as derived from a particular cancer type (e.g., hepatocellular carcinoma).

A first and second assay can serve to screen for a condition of a subject. Various combinations of assays are contemplated. For example, the first assay can assess copy number aberrations and the second assay can assess methylation status. The first assay can assess copy number aberrations and the second assay can assess fragment size. The first assay can assess copy number aberrations and the second assay can comprise analyzing an endpoint. The first assay can assess copy number aberrations and the second assay can comprise detecting mutations.

The first assay can assess fragment size and the second assay can assess copy number variation. The first assay can assess fragment size and the second assay can assess methylation status. The first assay can assess fragment size and the second assay can comprise analyzing an endpoint. The first assay can assess fragment size and the second assay can comprise detecting mutations.

The first assay can assess methylation and the second assay can assess copy number variation. The first assay can assess methylation status and the second assay can assess fragment size. The first assay can assess methylation status and the second assay can comprise analyzing an endpoint. The first assay can assess methylation status and the second assay can comprise detecting mutations.

The first assay can comprise analyzing an endpoint and the second assay can assess copy number variation. The first assay can comprise an endpoint and the second assay can assess fragment size. The first assay can comprise analyzing an endpoint and the second assay can assess methylation status. The first assay can comprise analyzing an endpoint and the second assay can comprise detecting mutations.

The first assay can comprise detecting mutations and the second assay can assess copy number variation. The first assay can comprise detecting mutations and the second assay can assess fragment size. The first assay can comprise detecting mutations and the second assay can assess methylation status. The first assay can comprise detecting mutations and the second assay can comprise analyzing an endpoint.

The first and second assays can comprise the same assay or analysis, but can be performed using different read depths. For example, the first assay can comprise sequencing nucleic acids at a lower read depth than the second assay. In some embodiments, the first assay is performed using a shallow read depth, such as 30 million reads, and the second assay is performed at a deeper read depth. For example, the first assay can assess copy aberrations using a "shallow" number of sequence reads and the second assay can assess copy number aberration using a "deeper" number of sequence reads. The second assay can be selected and performed in light of the results of the first assay. A positive predictive value for the presence of a condition based on the first and second assay can be greater than the positive predictive value for the presence of the condition based on the first assay alone.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

As used herein, the term "about" a number refers to a range spanning that number plus or minus 10% of that number. The term "about" a range refers to that range minus 10% of its lowest value and plus 10% of its greatest value.

As used here, the terms "comprise," "comprises," "comprising," "include," "includes," and "including" are interchangeable and not intended to be limiting, and refer to the nonexclusive presence of the recited element, leaving open the possibility that additional elements are present.

As used herein, the term "subject", can refer to any individual or patient to which the subject methods are performed. In some embodiments, the subject is human, although as will be appreciated by those in the art, the subject can be another animal. Other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, "obtaining" a nucleic acid sample can refer to receiving an isolated nucleic acid sample, as well as receiving a raw human sample, for example, and isolating nucleic acids therefrom.

The term "true positive" (TP), as used in the present disclosure, can refer to a subject having a condition. "True positive" can refer to a subject that has a tumor, a cancer, a precancerous condition (e.g., a precancerous lesion), a localized or a metastasized cancer, or a non-malignant disease. "True positive" can refer to a subject having a condition, and can be identified as having the condition by an assay or method of the present disclosure.

The term "true negative" (TN), as used in the present disclosure, can refer to a subject that does not have a condition or does not have a detectable condition. True negative can refer to a subject that does not have a disease or a detectable disease, such as a tumor, a cancer, a precancerous condition (e.g., a precancerous lesion), a localized or a metastasized cancer, a non-malignant disease, or a subject that is otherwise healthy. True negative can refer to a subject that does not have a condition or does not have a detectable condition, or is identified as not having the condition by an assay or method of the present disclosure.

The term "false positive" (FP), as used in the present disclosure, can refer to a subject that does not have a condition. False positive can refer to a subject that does not have a tumor, a cancer, a precancerous condition (e.g., a precancerous lesion), a localized or a metastasized cancer, a non-malignant disease, or is otherwise healthy. The term false positive can refer to a subject that does not have a condition, but is identified as having the condition by an assay or method of the present disclosure.

The term "false negative" (FN), as used in the present disclosure, can refer to a subject that has a condition. False negative can refer to a subject that has a tumor, a cancer, a precancerous condition (e.g., a precancerous lesion), a localized or a metastasized cancer, or a non-malignant disease. The term false negative can refer to a subject that has a condition, but is identified as not having the condition by an assay or method of the present disclosure.

The terms "sensitivity" or "true positive rate" (TPR), as used in the present disclosure, can refer to the number of true positives divided by the sum of the number of true positives and false negatives. Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

The terms "specificity" or "true negative rate" (TNR), as used in the present disclosure, can refer to the number of true negatives divided by the sum of the number of true negatives and false positives. Specificity can characterize the ability of an assay or method to correctly identify a proportion of the population that truly does not have a condition. For example, specificity can characterize the ability of a method to correctly identify the number of subjects within a population not having cancer. In another example, specificity can characterize the ability of a method to correctly identify one or more markers indicative of cancer.

"Negative predictive value" or "NPV" can be calculated by TN/(TN+FN) or the true negative fraction of all negative test results. Negative predictive value can be inherently impacted by the prevalence of a condition in a population and pre-test probability of the population intended to be tested.

"Positive predictive value" or "PPV" can be calculated by TP/(TP+FP) or the true positive fraction of all positive test results. PPV can be inherently impacted by the prevalence of a condition in a population and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which is entirely incorporated herein by reference.

The term "mutation," as used herein, can refer to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation can occur in a nucleic acid. In a particular example, a mutation can be a detectable change in one or more deoxyribonucleic acids or fragments thereof. A mutation can refer to one or more nucleotides that are added, deleted, substituted for, inverted, or transposed to a new position in a nucleic acid. A mutation can be a spontaneous mutation or an experimentally induced mutation.

A mutation in the sequence of a particular tissue can be an example of a "tissue-specific allele." For example, a tumor can have a mutation that results in an allele at a locus that does not occur in normal cells.

The terms "control," "control sample," "reference," "reference sample," "normal," and "normal sample" can be used to describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, for example, a reference genome that can be used to map sequence reads obtained from sequencing a sample from the subject. A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

The phrase "healthy," as used herein, can refer to a subject possessing good health. A healthy subject can demonstrate an absence of any malignant or non-malignant disease. A "healthy individual" can have other diseases or conditions, unrelated to the condition being assayed, which can normally not be considered "healthy."

The term "sample," "biological sample" can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

The term "fragment" (e.g., a DNA fragment), as used herein, can refer to a portion of a polynucleotide or polypeptide sequence that comprises at least 3 consecutive nucleotides. A nucleic acid fragment can retain the biological activity and/or some characteristics of the parent polynucleotide.

The terms "cancer" or "tumor" can refer to an abnormal mass of tissue wherein the growth of the mass surpasses or is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites.

The term "level of cancer" can refer to whether cancer exists (i.e., presence or absence), a stage of a cancer, a size of tumor, presence or absence of metastasis, the total tumor burden of the body, and/or other measure of a severity of a cancer (e.g., recurrence of cancer). The level of cancer can be a number or other indicia, such as symbols, alphabet letters, and colors. The level can be zero. The level of cancer can also include premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance of cancer metastasizing. Detection can comprise 'screening' or can comprise checking if someone, with suggestive features of cancer (e.g., symptoms or other positive tests), has cancer. A "level of pathology" can refer to level of pathology associated with a pathogen, where the level can be as described above for cancer. When the cancer is associated with a pathogen, a level of cancer can be a type of a level of pathology.

The term "assay" can refer to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragment). An assay or method can have a particular sensitivity and/or specificity, and their relative usefulness as a diagnostic tool can be measured using ROC-AUC statistics.

"Cancer-associated changes" or "cancer-specific changes" can include cancer-derived mutations (including single nucleotide mutations, deletions or insertions of nucleotides, deletions of genetic or chromosomal segments, translocations, inversions), amplification of genes, virus-associated sequences (e.g., viral episomes, viral insertions, viral DNA that can be infected into a cell and subsequently released by the cell, and circulating or cell-free viral DNA), aberrant methylation profiles or tumor-specific methylation signatures, aberrant cell-free nucleic acid (e.g., DNA) size profiles, aberrant histone modification marks and other epigenetic modifications, and locations of the ends of cell-free DNA fragments that are cancer-associated or cancer-specific.

The term "random sequencing," as used herein can refer to sequencing whereby nucleic acid fragments sequenced have not been specifically identified or predetermined before the sequencing procedure. Sequence-specific primers to target specific gene loci are not required. In some embodiments, adapters are added to the end of a nucleic acid fragment, and primers for sequencing are attached (e.g., hybridized) to the adapters. Thus, any fragment can be sequenced with the same primer, e.g., that attaches to a same universal adapter, and thus the sequencing can be random. Massively parallel sequencing can include using random sequencing.

A "sequence read" (or "sequencing read") can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

The term "sequencing depth" can refer to the number of times a locus is covered by a sequence read aligned to the locus. The locus can be as small as a nucleotide, or as large as a chromosome arm, or as large as an entire genome. Sequencing depth can be expressed as "Yx", e.g., 50×, 100×, etc., where can "Y" refer to the number of times a locus is covered with a sequence read. Sequencing depth can also be applied to multiple loci, or the whole genome, in which case Y can refer to the mean number of times a loci or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

The term "sequencing breadth" can refer to what fraction of a particular reference genome (e.g., human reference genome) or part of the genome has been analyzed. The denominator of the fraction can be a repeat-masked genome, and thus 100% can correspond to all of the reference genome minus the masked parts. A repeat-masked genome can refer to a genome in which sequence repeats are masked (e.g., sequence reads align to unmasked portions of the genome). Any parts of a genome can be masked, and thus one can focus on any particular part of a reference genome. Broad sequencing can refer to sequencing and analyzing at least 0.1% of the genome.

A "methylome" can be a measure of an amount of DNA methylation at a plurality of sites or loci in a genome. The methylome can correspond to all of a genome, a substantial part of a genome, or relatively small portion(s) of a genome. A "tumor methylome" can be a methylome of a tumor of a subject (e.g., a human). A tumor methylome can be determined using tumor tissue or cell-free tumor DNA in plasma. A tumor methylome can be one example of a methylome of interest. A methylome of interest can be a methylome of an organ that can contribute nucleic acid, e.g., DNA into a bodily fluid (e.g., a methylome of brain cells, a bone, lungs, heart, muscles, kidneys, etc.). The organ can be a transplanted organ.

A "plasma methylome" can be the methylome determined from plasma or serum of an animal (e.g., a human). A plasma methylome can be an example of a cell-free methylome since plasma and serum can include cell-free DNA. A plasma methylome can be an example of a mixed methylome since it can be a mixture of tumor/patient methylome. A "cellular methylome" can be a methylome determined from cells (e.g., blood cells or tumor cells) of a subject, e.g., a patient. A methylome of blood cells can be called a blood cell methylome (or blood methylome).

The "methylation index" for each genomic site (e.g., a CpG site) can refer to the proportion of sequence reads showing methylation at the site over the total number of reads covering that site. The "methylation density" of a region can be the number of reads at sites within a region showing methylation divided by the total number of reads covering the sites in the region. The sites can have specific characteristics, (e.g., the sites can be CpG sites). The "CpG methylation density" of a region can be the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of unconverted cytosines (which can correspond to methylated cytosine) at CpG sites as a proportion of all CpG sites covered by sequence reads mapped to the 100-kb region. This analysis can also be performed for other bin sizes, e.g., 50-kb or 1-Mb, etc. A region can be an entire genome or a chromosome or part of a chromosome (e.g., a chromosomal arm). A methylation index of a CpG site can be the same as the methylation density for a region when the region only includes that CpG site. The "proportion of methylated cytosines" can refer the number of cytosine sites, "C's," that are shown to be methylated (for example unconverted after bisulfite conversion) over the total number of analyzed cytosine residues, i.e., including cytosines outside of the CpG context, in the region. The methylation index, methylation density and proportion of methylated cytosines are examples of "methylation levels."

A "methylation profile" (also called methylation status) can include information related to DNA methylation for a region. Information related to DNA methylation can include a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes can refer to the addition of a methyl group to position 5 of the heterocyclic ring of cytosine (i.e., to produce 5-methylcytosine) among CpG dinucleotides. Methylation of cytosine can occur in cytosines in other sequence contexts, for example 5'-CHG-3' and 5'-CHH-3', where H is adenine, cytosine or thymine. Cytosine methylation can also be in the form of 5-hydroxymethylcytosine. Methylation of DNA can include methylation of non-cytosine nucleotides, such as N6-methyladenine.

The terms "size profile" and "size distribution" can relate to the sizes of DNA fragments in a biological sample. A size profile can be a histogram that provides a distribution of an amount of DNA fragments at a variety of sizes. Various statistical parameters (also referred to as size parameters or just parameter) can distinguish one size profile to another. One parameter can be the percentage of DNA fragment of a particular size or range of sizes relative to all DNA fragments or relative to DNA fragments of another size or range.

An "informative cancer DNA fragment" or an "informative DNA fragment" can correspond to a DNA fragment bearing or carrying any one or more of the cancer-associated or cancer-specific change or mutation, or a particular ending-motif (e.g., a number of nucleotides at each end of the DNA fragment having a particular sequence).

An "ending position" or "end position" (or just "end") can refer to the genomic coordinate or genomic identity or nucleotide identity of the outermost base, i.e., at the extremities, of a cell-free DNA molecule, e.g., plasma DNA molecule. The end position can correspond to either end of a DNA molecule. In this manner, if one refers to a start and end of a DNA molecule, both can correspond to an ending position. In some cases, one end position is the genomic coordinate or the nucleotide identity of the outermost base on one extremity of a cell-free DNA molecule that is detected or determined by an analytical method, e.g., massively parallel sequencing or next-generation sequencing, single molecule sequencing, double- or single-stranded DNA sequencing library preparation protocols, polymerase chain reaction (PCR), or microarray. In some cases, such in vitro techniques can alter the true in vivo physical end(s) of the cell-free DNA molecules. Thus, each detectable end can represent the biologically true end or the end is one or more nucleotides inwards or one or more nucleotides extended from the original end of the molecule e.g., 5' blunting and 3' filling of overhangs of non-blunt-ended double stranded DNA molecules by the Klenow fragment. The genomic identity or genomic coordinate of the end position can be derived from results of alignment of sequence reads to a human reference genome, e.g., hg19. It can be derived from a catalog of indices or codes that represent the original coordinates of the human genome. It can refer to a position or nucleotide identity on a cell-free DNA molecule that is read by but not limited to target-specific probes, mini-sequencing, DNA amplification. The term "genomic position" can refer to a nucleotide position in a polynucleotide (e.g., a gene, a plasmid, a nucleic acid fragment, a viral DNA fragment). The term "genomic position" is not limited to nucleotide positions within a genome (e.g., the haploid set of chromosomes in a gamete or microorganism, or in each cell of a multicellular organism).

A "preferred end" (or "recurrent ending position") can refer to an end that is more highly represented or prevalent (e.g., as measured by a rate) in a biological sample having a physiological or pathological (disease) state (e.g., cancer) than a biological sample not having such a state or than at different time points or stages of the same pathological or physiological state, e.g., before or after treatment. A preferred end can have an increased likelihood or probability for being detected in the relevant physiological or pathological state relative to other states. The increased probability can be compared between the pathological state and a non-pathological state, for example in patients with and without a cancer and quantified as likelihood ratio or relative probability. The likelihood ratio can be determined based on the probability of detecting at least a threshold number of preferred ends in the tested sample or based on the probability of detecting the preferred ends in patients with such a condition than patients without such a condition. Examples for the thresholds of likelihood ratios include but are not limited to 1.1, 1.2, 1.3, 1.4, 1.5, 1.6, 1.8, 2.0, 2.5, 3.0, 3.5, 4.0, 4.5, 5, 6, 8, 10, 20, 40, 60, 80 and 100. Such likelihood ratios can be measured by comparing relative abundance values of samples with and without the relevant state. Because the probability of detecting a preferred end in a relevant physiological or disease state can be higher, such preferred ending positions can be seen in more than one individual with that same physiological or disease state. With the increased probability, more than one cell-free DNA molecule can be detected as ending on a same preferred ending position, even when the number of cell-free DNA molecules analyzed is far less than the size of the genome. Thus, the preferred or recurrent ending positions can also referred to as the "frequent ending positions." A quantitative threshold sometimes requires that ends be detected at least multiple times (e.g., 3, 4, 5, 6, 7, 8, 9, 10, 15, 20, or 50) within the same sample or same sample aliquot to be considered as a preferred end. A relevant physiological state can include a state when a person is healthy, disease-free, or free from a disease of interest. Similarly, a "preferred ending window" can correspond to a contiguous set of preferred ending positions.

A "relative abundance" can refer to a ratio of a first amount of nucleic acid fragments having a particular characteristic (e.g., a specified length, ending at one or more specified coordinates/ending positions, or aligning to a particular region of the genome) to a second amount nucleic acid fragments having a particular characteristic (e.g., a specified length, ending at one or more specified coordinates/ending positions, or aligning to a particular region of the genome). In one example, relative abundance can refer to a ratio of the number of DNA fragments ending at a first set of genomic positions to the number of DNA fragments ending at a second set of genomic positions. In some aspects, a "relative abundance" can be a type of separation value that relates an amount (one value) of cell-free DNA molecules ending within one window of genomic position to an amount (other value) of cell-free DNA molecules ending within another window of genomic positions. The two windows can overlap, but can be of different sizes. In other implementations, the two windows may not overlap. Further, the windows can be of a width of one nucleotide, and therefore be equivalent to one genomic position.

A "rate" of nucleic acid molecules (e.g., DNA or RNA) ending on a position can relate to how frequently a nucleic acid molecule ends on the position. The rate can be based on a number of nucleic acid molecules that end on the position normalized against a number of nucleic acid molecules analyzed. The rate can be based on a number of nucleic acid molecules that end on the position normalized against a number of nucleic acid molecules that end on a different position. The rate can be based on a number of nucleic acid molecules from a first sample that end on the position normalized against a number of nucleic acid molecules from a second sample (e.g., a reference sample) that end on the position. The rate can be based on a number of nucleic acid molecules from a first sample that end on a first set of positions (e.g., genomic positions) normalized against a number of nucleic acid molecules from a second sample (e.g., a reference sample) that end on a second set of positions. Accordingly, the rate can correspond to a frequency of how many nucleic acid molecules end on a position, and in some cases does not relate to a periodicity of positions having a local maximum in the number of nucleic acid molecules ending on the position.

A "calibration sample" can correspond to a biological sample whose tissue-specific nucleic acid fraction is known or determined via a calibration method, e.g., using an allele specific to the tissue. As another example, a calibration sample can correspond to a sample from which preferred ending positions can be determined. A calibration sample can be used for both purposes.

A "calibration data point" can include a "calibration value" and a measured or known proportional distribution of the nucleic acid of interest (i.e., DNA of particular tissue type). The calibration value can be a relative abundance as determined for a calibration sample, for which the proportional distribution of the tissue type can be known. The calibration data points can be defined in a variety of ways, e.g., as discrete points or as a calibration function (also called a calibration curve or calibration surface). The calibration function can be derived from additional mathematical transformation of the calibration data points.

The term "classification" can refer to any number(s) or other characters(s) that are associated with a particular property of a sample. For example, a "+" symbol (or the word "positive") can signify that a sample is classified as having deletions or amplifications. In another example, the term "classification" can refer to an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

A "tissue" can correspond to a group of cells that group together as a functional unit. More than one type of cell can be found in a single tissue. Different types of tissue can consist of different types of cells (e.g., hepatocytes, alveolar cells or blood cells), but also can correspond to tissue from different organisms (mother vs. fetus) or to healthy cells vs. tumor cells. The term "tissue" can refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

The section headings used herein are for organizational purposes only and are not to be construed as limiting the subject matter described.

II. ASSAYS

The following illustrates various assays that can be used in the methods of the present disclosure. Any of the following assays can be used as a first assay, second assay, third assay, etc. or a combination of any of the above. For example, the first assay can be a qPCR assay and the second assay can be a NGS assay (e.g., any assay that performs a next-generation sequencing assay). Examples of NGS assays include assays that detect copy number aberrations, methylation profiles, cfDNA fragment size, mutations, and assays that assess fragment endpoints.

In a particular example, a first assay for a first marker or a first set of markers can have a sensitivity indicative of a tumor, and the second assay for a second marker or second set of markers can have a specificity indicative of a tumor. The first marker and the second marker can be the same or different. The first set of markers and the second set of markers can be the same or different. The first assay and the second assay can be the same or different.

A second assay can be performed hours, days, or weeks after the first assay. In one embodiment, a second assay can be performed immediately after the first assay. In other embodiments, a second assay can be performed within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after the first assay. In a particular example, the second assay can be performed within 2 weeks of the first sample. A second assay can be used to improve the specificity with which a tumor can be detected in a patient. The time between performing the first assay and the second assay can be determined experimentally. In some embodiments, a method provided herein can comprise 2 or more assays, and the 2 or more assays use the same sample (e.g., a single sample is obtained from a subject, e.g., a patient, prior to performing the first assay, and is preserved for a period of time until performing the second assay). For example, two tubes of blood can be obtained from a subject at the same time. A first tube can be used for a first assay. The second tube can be used only if results from the first assay from the subject are positive. The sample can be preserved using any method known to a person having skill in the art (e.g., cryogenically). This preservation can be beneficial in certain situations, for example, in which a subject can receive a positive test result (e.g., the first assay is indicative of cancer), and the patient can rather not wait until performing the second assay, opting rather to seek a second opinion.

The time between obtaining a sample and performing an assay can be optimized to improve the sensitivity and/or specificity of the assay or method. In some embodiments, a sample can be obtained immediately before performing an assay (e.g., a first sample is obtained prior to performing the first assay, and a second sample is obtained after performing the first assay but prior to performing the second assay). In some embodiments, a sample can be obtained, and stored for a period of time (e.g., hours, days or weeks) before performing an assay. In some embodiments, an assay can be performed on a sample within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after obtaining the sample from the subject.

The time between performing an assay (e.g., a first assay or a second assay) and determining if the sample includes a marker or a set of markers indicative of the tumor can be varied. In some instances, the time can be optimized to improve the sensitivity and/or specificity of the assay or method. In some embodiments, determining if the sample includes a marker or a set of markers indicative of a tumor can occur within at most 0.1 hour, 0.5 hours, 1 hour, 2 hours, 4 hours, 8 hours, 12 hours, 24 hours, 2 days, 3 days, 4 days, 5 days, 6 days, 1 week, 2 weeks, 3 weeks, or 1 month of performing the assay.

A. Detecting Copy Number Aberration

In some embodiments, an assay includes determining whether a nucleic acid sequence imbalance exists within a biological sample obtained from a subject. This determination can be done by using a parameter of an amount of a clinically-relevant chromosomal region in relation to other non-clinically-relevant chromosomal regions (such as background or control regions) within a biological sample. In one aspect, an amount of a chromosomal region is determined from a sequencing of nucleic acid molecules in the sample. Nucleic acid molecules of the biological sample are sequenced, such that at least a fraction of the genome is sequenced. One or more cutoff values can be chosen for determining whether a change compared to a reference quantity exists (i.e. an imbalance), for example, with regards to the ratio of amounts of two chromosomal regions (or sets of regions).

The assay can include analyzing a sample for deletions or amplifications in one or more chromosomal regions associated with a disease or condition, including cancer. The biological sample can include nucleic acid molecules. A portion of the nucleic acid molecules contained in the biological sample are sequenced.

In some embodiments, both ends of nucleic acids can be sequenced. The ends of the sequence can be used to provide a length of each sequence or fragment. For example, a comparison of both ends of a fragment to a reference sequence, such as a genome, can be used to determine the length of the fragment.

Based on the sequencing, a first amount of a first chromosomal region can be determined from sequences identified as originating from the first chromosomal region. A second amount of one or more second chromosomal regions is determined from sequences identified as originating from one of the second chromosomal regions.

Further, a parameter from the first amount and the second amount is then compared to one or more cutoff values. Based on the comparison, a classification of whether a deletion or an amplification associated with cancer exists for the first chromosomal region is determined.

The change detected relative to the reference quantity can be any deviation (upwards or downwards) in the relation of the clinically relevant nucleic acid sequence to the other non-clinically-relevant sequences. Thus, the reference state can be a ratio or other quantity, and a measured state signifying a change can be any ratio or other quantity that differs from the reference quantity as determined by the one or more cutoff values.

The clinically relevant chromosomal region (also called a clinically relevant nucleic acid sequence) and the background nucleic acid sequence can come from a first type of cells and from one or more second types of cells. For example, cancer nucleic acid sequences originating from cancer cells can be present in a biological sample, such as plasma, which contains a background of normal nucleic acid sequences originating from non-cancerous cells. In one embodiment, the cutoff value is determined based at least in part on a percentage of the first type of cells in a biological sample. Note the percentage of cancer sequences in a sample can be determined by any cancer-derived loci and not limited to measuring the clinically-relevant nucleic acid sequences. In another embodiment, the cutoff value is determined at least in part on the percentage of tumor sequences in a biological sample, such as plasma, serum, saliva or urine, which contains a background of nucleic acid sequences derived from the non-malignant cells within the body.

In some aspects, determining the amount of a clinically relevant nucleic acid present in a sample comprises locating the DNA sequence of the nucleic acid on a reference genome. For example, a bioinformatics procedure can be used to locate each of these DNA sequences to the human genome. A proportion of such sequences can be discarded from subsequent analysis because they are present in the repeat regions of the human genome, or in regions subjected to inter-individual variations. These variations can include inter-individual copy number variations, which can be unrelated to the presence of cancer. An amount of the chromosome or locus of interest and of one or more other chromosomes can thus be determined.

A second amount of a second chromosome or locus can be determined from sequences identified as originating from a different chromosome or locus than the first chromosome or locus. In one embodiment, the second chromosome or locus can be any of the other chromosomes or loci besides the first one (i.e. the one being tested). In another embodiment, the second chromosome or locus is just a single other chromosome or locus.

In some aspects, detecting the presence of a copy number aberration comprises counting the number of sequenced tags (examples include unique identifiers, degenerate base pair sequences, and barcodes which can be used to label cfDNA molecules), the number of sequenced nucleotides (basepairs) or the accumulated lengths of sequenced nucleotides (basepairs) originating from particular chromosome(s) or chromosomal regions.

In some aspects, a parameter of a genomic locus potentially comprising a copy number aberration can be calculated from the results of the bioinformatics procedure. For example, a fractional representation of the clinically relevant nucleic acids to the background nucleic acids can be determined. Examples of background nucleic acids include segments or fragments derived from the same chromosome as the relevant nucleic acid, segments derived from a different chromosome as the relevant nucleic acid, the number of reads in the sample, the number of relevant nucleic acids in a different or control sample, the average number of relevant nucleic acids in a plurality of control samples, a threshold value, and combinations thereof.

The parameter can be compared to one or more cutoff values to determine a result of the assay. The cutoff values can be determined from any number of suitable ways. Such ways include Bayesian type likelihood method, sequential probability ratio testing (SPRT), false discovery, confidence interval, receiver operating characteristic (ROC). Such comparisons can be used to determine whether a copy number aberration exists and/or detect the presence of cancer in the sample.

In some embodiments, the dosage imbalance of a particular chromosome or chromosomal region can be quantitatively determined. This can be achieved with a variety of sequencing depths (e.g., shallow or deep sequencing) and each nucleic acid in a genome need not be sequenced in order to detect an imbalance. For example, the dosage imbalance of the chromosome or chromosomal regions can be inferred from the percentage representation of the locus among other mapable sequenced tags of the specimen using shallow sequencing. This can be contrasted from situations where the same pool of nucleic acids is sequenced multiple times to achieve high redundancy or several folds of coverage whereby each nucleic acid species can be sequenced multiple times. In such situations, the number of times a particular nucleic acid species have been sequenced relative to that of another nucleic acid species can correlate with their relative concentrations in the original sample. The sequencing cost can increase with the number of fold coverage required to achieve accurate representation of the nucleic acid species.

Quantitation can take into account the relative sizes of a particular chromosome or locus and a control. Comparing the relative size clinically relevant nucleic acids to the background nucleic acids can generate a normalized frequency of clinically relevant nucleic acids. The normalized frequency can allow for the detection of copy number aberrations and the degree of change can be dependent on the fractional concentration of the clinically relevant nucleic acids.

In some embodiments, cell free nucleic acids are labeled with a barcode or a degenerate base pair sequence. Such barcodes or degenerate base pair sequences can serve as a unique identifier (UID) for a particular fragment found in a sample. Tagging the fragments with UIDs can allow for the discrimination between fragments that contain similar sequences but that originated from different template nucleic acid molecules. In some embodiments, quantification of a particular chromosome or locus comprises counting the number of UIDs associated with that particular chromosome or locus. Both the clinically relevant nucleic acids and the background nucleic acids can be quantified using this technique. The relative amounts of nucleic acids derived from a particular chromosome or region can be determined by comparison to background nucleic acids, as described above.

In some embodiments, clinically relevant nucleic acids can be quantified by counting the number of species of nucleic acids that are derived from a particular locus or chromosome. For example, the identification of the endpoints of a fragment can be used to discriminate a particular fragment from other fragments derived from the same genomic locus or chromosome with different endpoints. In some embodiments, quantification of a particular chromosome or locus comprises counting the number of species with unique endpoints associated with that particular chromosome or locus. Both the clinically relevant nucleic acids and the background nucleic acids can be quantified using this technique. The relative amounts of nucleic acids derived from a particular chromosome or region can be determined by comparison to background nucleic acids, as described above.

In one embodiment, the number of sequences corresponding to a particular size or size range that correspond to a particular chromosome or locus can be counted. The number of aligned sequenced tags can be counted and sorted according to chromosomal location. Gains or losses of chromosomal regions or whole chromosomes can be determined by comparing the tag counts with the expected chromosome or locus size in the reference genome or that of a non-disease representative specimen. As paired end sequencing allows one to deduce the size of the original nucleic acid fragment, one example includes counting of the number of paired sequenced tags corresponding to nucleic acid fragments of a specified size, such as <300 bp, <200 bp or <100 bp.

In some embodiments, the fraction of the nucleic acid pool that is sequenced can be sub-selected prior to sequencing. For example, hybridization based techniques such as oligonucleotide arrays can be used to first sub-select for nucleic acid sequences from certain chromosomes, e.g. a region associated with cancer. Another example is that a certain sub-population of nucleic acid sequences from the sample pool is sub-selected or enriched prior to sequencing. For example, it has been reported that circulating tumor DNA molecules can be comprised of shorter fragments than the background cfDNA molecules. Thus, one may use one or more methods known to those of skill in the art to fractionate the nucleic acid sequences in the sample according to molecule size, e.g. by gel electrophoresis or size exclusion columns or by microfluidics-based approach. In one embodiment, a portion or subset of the pre-selected pool of nucleic acids is sequenced randomly.

Exemplary methods and embodiments of determining copy number aberrations are described in WO 2013/132305 and U.S. application Ser. No. 12/614,350 (Publication No. US2010-0112590), the contents of each of which are herein incorporated by reference in their entirety.

The following table describes exemplary chromosomal aberrations seen in various types of cancers:

| Cancer | Gain | Loss | References |
|---|---|---|---|
| Colorectal | 7p, 7q, 8q, 11q, 13q, and 20q | 5q, 8p, 17p, 18p, 18q and 20p | (Nakao et al. Carcinogenesis 2004; 25:1345-1357.) (Tsafrir et al. Cancer Res 2006; 66: 2129-2137) |
| Breast | 1q, 6p, 8q, 11q, 16p, 17q, 19, and 20q | 6q, 13q, 16q, 17p, and 22q | (Tirkkonen et al. Gene Chromosome Canc 1998; 21: 177-184) (Richard et al. Int J Cancer 2000; 89: 305-310) (Pinkel et al. Nat Genet 1998; 20: 207-211) (Persson et al. Gene Chromosome Canc 1999; 25: 115-122) (Nishizaki et al. Int J Cancer 1997; 74:513-517) |
| Lung | 1q, 3q, 5p, and 8q | 3p, 6q, 8p, 9p, 13q, and 17p | (Berrieman et al. Brit J Cancer 2004; 90:900-905) (Luk et al. Cancer Genet Cytogen 2001; 125:87-99) (Petersen et al. Cancer Res 1997; 57:2331-2335) (Pei et al. Gene Chromosome Canc 2001; 31:282-287) |
| HCC | 1q, 8q, 17q, and 20q | 4q, 6q, 8p, 13q, 16q and 17p | (Kusano et al. Cancer 2002; 94:746-751) (Laurent-Puig et al. Gastroenterology 2001; 120:1763-1773) (Moinzadeh et al. Brit J Cancer 2005; 92:93 5-941) |
| Ovarian | 20q, 3q, 1q, 8q, 12p, 11q, and 17q | Xp, 18q, 4Q, 9p, and 13q | Taetle et al. Gene Chromosome Canc 1999; 25: 290-300) (Schraml et al. Am J Pathol 2003; 163:985-992) (Sonoda et al. Gene Chromosome Canc 1997; 20:320-328) |

B. Methylation Profile

In another embodiment, an assay (e.g., first assay or a second assay) can comprise performing methylation-aware sequencing, or sequencing cell-free nucleic acid molecules to determine a methylation status at one or more genomic locations. Exemplary techniques and embodiments related to, e.g., determining a methylation status, can be found in PCT/AU2013/001088, PCT/GB2007/003674, and PCT/CN2015/08442, and U.S. Patent Application Publication Nos. 20160340740 and 20170121767, each of which are entirely incorporated herein by reference. Qualitative changes in the methylation profile can be reflected among the plasma methylome data. Plasma DNA molecules originating from genes that are hypermethylated only in cancer cells can show hypermethylation in plasma of a cancer patient when compared with plasma DNA molecules originating from the same genes but in a sample of a healthy control. Because aberrant methylation occurs in most cancers, the methods herein described can be applied to the detection of all forms of malignancies with aberrant methylation, for example, malignancies in, but not limited to, the lung, breast, colorectum, prostate, nasopharynx, stomach, testes, skin, nervous system, bone, ovary, liver, hematologic tissues, pancreas, uterus, kidney, lymphoid tissues, etc. The malignancies can be of a variety of histological subtypes, for example, carcinomas, adenocarcinomas, sarcomas, fibroadenocarcinoma, neuroendocrine, and undifferentiated.

Tumor-derived DNA molecules can be distinguished from the background non-tumor-derived DNA molecules because the overall short size profile of tumor-derived DNA can be accentuated for DNA molecules originating from loci with tumor-associated aberrant hypomethylation which can have an additional effect on the size of the DNA molecule. Also, tumor-derived plasma DNA molecules can be distinguished from the background non-tumor-derived plasma DNA molecules using multiple characteristic features that are associated with tumor DNA, including but not limited to single nucleotide variants, copy number gains and losses, translocations, inversions, aberrant hyper- or hypo-methylation and size profiling. As all of these changes can occur independently, the combined use of these features can provide additive advantage for the sensitive and specific detection of cancer DNA in plasma.

The methylation densities of the pre-operative plasma DNA can be lower than those of the non-malignant tissues in the cancer patient. This can result from the presence of DNA from the tumor tissue which was hypomethylated. This lower plasma DNA methylation density can be used as a biomarker for the detection and monitoring of cancer. For cancer monitoring, if a cancer is progressing, then there can be an increased amount of cancer-derived DNA in plasma with time. In this example, an increased amount of circulating cancer-derived DNA in plasma can lead to a further reduction in the plasma DNA methylation density on a genome wide level.

Conversely, if a cancer responds to treatment, then the amount of cancer-derived DNA in plasma can decrease with time. In this example, a decrease in the amount of cancer-derived DNA in plasma can lead to an increase in the plasma DNA methylation density. For example, if a lung cancer patient with epidermal growth factor receptor mutation has been treated with a targeted therapy, e.g., tyrosine kinase inhibition, then an increase in plasma DNA methylation density can signify a response. Subsequently, the emergence of a tumor clone resistant to tyrosine kinase inhibition can be associated with a decrease in plasma DNA methylation density which can indicate a relapse.

Plasma methylation density measurements can be performed serially and the rate of change of such measurements can be calculated and used to predict or correlate with clinical progression or remission or prognosis. For selected genomic loci which are hypermethylated in cancer tissues but hypomethylated in normal tissues, e.g., the promoter regions of a number of tumor suppressor genes, the relationship between cancer progression and favorable response to treatment can be opposite to the patterns described above.

Plasma methylation density values beyond, for example lower than, a defined cutoff based on the reference values can be used to assess if a subject's plasma has tumor DNA or not. To detect the presence of hypomethylated circulating tumor DNA, the cutoff can be defined as lower than the 5th or 1st percentiles of the values of the control population, or based on a number of standard deviations, for example, 2 or 3 standard deviations (SDs), below the mean methylation density values of the controls, or based on determining a multiple of the median (MoM). For hypermethylated tumor DNA, the cutoff can be defined as higher than the 95th or 99th percentile of the values of the control population, or based on a number of standard deviations, for example, 2 or 3 SDs, above the mean methylation density values of the controls, or based on determining a multiple of the median (MoM). In one embodiment, the control population can be matched in age to the test subject. The age matching does not need to be exact and can be performed in age bands (e.g., 30 to 40 years, for a test subject of 35 years).

To assess if a tested subject has cancer, the result of the tested subject can be compared to the values of a reference group. In one embodiment, the reference group can comprise of a number of healthy subjects. In another embodiment, the reference group can comprise of subjects with non-malignant conditions, for example, chronic hepatitis B infection or cirrhosis. The difference in the methylation densities between the tested subject and the reference group can then be quantified.

In one embodiment, a reference range can be derived from the values of the control group. Then deviations in the result of the tested subject from the upper or lower limits of the reference group can be used to determine if the subject has a tumor. This quantity can be affected by the fractional concentration of tumor-derived DNA in the plasma and the difference in the level of methylation between malignant and nonmalignant tissues. Higher fractional concentration of tumor-derived DNA in plasma can lead to larger methylation density differences between the test plasma sample and the controls. A larger degree of difference in the methylation level of the malignant and non-malignant issues can also be associated with larger methylation density differences between the test plasma sample and the controls. In yet another embodiment, different reference groups are chosen for test subjects of different age ranges.

In one embodiment, the genome or loci within a genome can be divided into a plurality of bins. In some embodiments the bins have a defined length or a defined boundary. In other embodiments, the bins do not have defined lengths or boundaries. In some embodiments, a mean and SD of the methylation densities of control subjects can be calculated for at least one bin. Then for the corresponding bin or bins, the difference between the methylation densities of the cancer patient, such as a patient with HCC, and the mean value of the control subjects can be calculated. In one embodiment, this difference can then be divided by the SD of the corresponding bin to determine the z-score. In other words, the z-score can represent the difference in methylation densities between the test and control plasma samples expressed as a number of SDs from the mean of the control subjects. A z-score >3 of a bin can indicate that the plasma DNA of the cancer patient is more hypermethylated than the control subjects by more than 3 SDs in that bin whereas a z-score of <−3 in a bin indicates that the plasma DNA of the cancer patient is more hypomethylated than the control subjects by more than 3 SDs in that bin.

The cutoff values of the number of bins can be determined using statistical methods. For example, approximately 0.15% of the bins can be expected to have a Z-score of <−3 based on a normal distribution. Therefore, the cutoff number of bins can be 0.15% of the total number of bins being analyzed. In other words, if a plasma sample from a subject shows more than 0.15% of bins with Z-scores <−3, there can be a source of hypomethylated DNA in plasma, namely cancer.

In yet another embodiment, the cutoff number can be determined by receiver operator characteristic (ROC) curve analysis by analyzing a number of cancer patients and individuals without cancer. In one embodiment, different thresholds can be used to classify different levels of disease status. A lower percentage threshold can be used to differentiate healthy status from benign conditions and a higher percentage threshold to differentiate benign conditions from malignancies.

Bins that are above or below a cutoff value can be classified as abnormal. The proportion or number of abnormal bins can be used to determine if the subject has cancer. Alternatively or in addition, the magnitude or the amount by which a bin deviates from a cutoff can be informative of a presence of cancer in the subject.

In other embodiments, other methods can be used to survey the methylation level of plasma DNA. For example, the proportion of methylated cytosine residues over the total content of cytosine residues can be determined using mass spectrometry (see e.g., M. L. Chen et al. 2013 Clin Chem; doi: 10.1373/clinchem.2012.193938) or massively parallel sequencing. However, as some cytosine residues cannot be in the CpG dinucleotide context, the proportion of methylated cytosine among total cytosine residuals can be relatively small when compared to methylation levels estimated in the context of CpG dinucleotides. The methylation level of the tissue and plasma samples obtained from the cancer patient as well as samples obtained from the healthy controls can be determined. The methylation levels can be measured in the context of CpGs, any cytosines, in 5'-CHG-3' and 5'-CHH-3' contexts using the genome-wide massively parallel sequencing data. H refers to adenine, thymine or cytosine residues.

In other embodiments, the methylation status of the plasma DNA can be determined by methods using antibodies against methylated cytosine, for example, methylated DNA immunoprecipitation (MeDIP). In yet another embodiment, the level of 5-hydroxymethylcytosine in plasma DNA can be determined. In this regard, a reduction in the level of 5-hydroxymethylcytosine can be an epigenetic feature of certain cancers, e.g., melanoma (see e.g., C. G. Lian, et al. 2012 Cell; 150: 1135-1146).

In another embodiment, this approach can be applied to other types of cancers. The plasma samples from patients a particular cancer can be analyzed. The plasma DNA of these subjects can be bisulfate-converted and sequenced using the Illumina HiSeq2000 platform for 50 bp at one end. Healthy control subjects can be used as a reference group for the analysis of these cancer patients. 50 bp of the sequence reads at one end can be used. The whole genome can be divided into 1 Mb bins. The mean and SD of methylation density can be calculated for each bin using the data from the reference group. Then the results of the cancer patients can be expressed as z-scores which represent the number of SDs from the mean of the reference group. A positive value can indicate that the methylation density of the test case is lower than the mean of the reference group, and vice versa.

In some embodiments, the methods include performing methylation haplotype analysis. Such methods can be used to determine whether the sample includes a methylation haplotype informative of the presence of cancer. In some embodiments, said methylation haplotype analysis comprises determining the combinatorial methylation status of a plurality of methylation sites in a nucleic acid molecule. In some embodiments, the method includes detecting the presence of a target nucleic acid in a mixture of nucleic acids. In some embodiments, said plurality of methylation sites comprises at least 2, at least 3, at least 4, at least 5, at least 10, at least 20, at least 40, at least 50, at least 100, at least 200, at least 300, at least 400, at least 500 or more than 500 methylation sites indicative of the presence of the target nucleic acid in the sample. The target nucleic acids can be present in low quantities or concentrations. To detect and quantify low abundance nucleic acids, such as circulating tumor DNA, marker regions in the genome in which there are major differences in methylation status between normal cells, such as normal cells in peripheral blood or other samples, and other cells of interest (such as cancer cells) can be analyzed. These can be the marker regions used for methylation status analysis. For example, a marker region containing 6 CpG sites might be completely unmethylated in whole blood, and fully methylated in cancer. A methylation haplotype can be the combinatorial (or linked) methylation status of multiple methylation sites (also called "sites" or "loci") in a single DNA molecule. Exemplary methods are disclosed in US Patent Application Publication No. 20160340740, which is incorporated herein in its entirety.

Methylation profiling can also be used to determine a tissue of origin of a cell-free nucleic acid. In some of such embodiments, the method includes determining the methylation status of at least four methylation sites on a continuous sequence of the cell-free DNA, the sequence comprising no more than 300 nucleotides, wherein a methylation status of each of the at least four methylation sites on the continuous sequence of the DNA characteristic of the cell type or tissue is indicative of death of the cell type or tissue. In HCC, for example, the nucleic acid being assessed can be derived from an albumin gene, including the promoter region of albumin. In some embodiments, the promoter of Albumin (ALB) is unmethylated in hepatocytes (and to some extent in kidney and pancreas) but is methylated elsewhere. The blood of healthy individuals can contain either no signal or a relatively high level of unmethylated albumin promoter DNA. In contrast, the blood of a patient with a liver condition, including a liver cancer such as HCC, can be methylated at a higher rate than a control. Exemplary methods are disclosed in US Patent Application Publication No. US20170121767, which is incorporated by reference in its entirety.

C. Fragmentation Patterns

In another embodiment, an assay (e.g., first assay or a second assay) can comprise performing an assay to analyze nucleic acid fragments. The assay can comprise next-generation sequencing.

Factors affecting the fragmentation pattern of cell-free DNA and the applications, including those in molecular diagnostics, of the analysis of cell-free DNA fragmentation patterns are described. Various applications can use a property of a fragmentation pattern to determine a proportional contribution of a particular tissue type, to determine a genotype of a particular tissue type. This includes tumor tissue in a sample from a cancer patient. Fragmentation patterns can also be used to identify preferred ending positions for a particular tissue type, which can then be used to determine a proportional contribution of a particular tissue type. In some embodiments, the preferred ending positions for a particular tissue can also be used to measure the absolute contribution of a particular tissue type in a sample. For example, the contribution of a particular tissue in a sample can be expressed as the number of genomes per unit volume, such as genomes per milliliter.

Examples of a classification of a proportional contribution include specific percentages, range of percentage, or whether the proportional contribution is above a specified percentage can be determined as a classification. For determining the classification of a proportional contribution, some embodiments can identify preferred ending positions corresponding to a particular tissue type (e.g., tumor tissue).

Such preferred ending positions can be determined in various ways. Examples include analyzing a rate at which cell-free DNA molecules end on genomic positions, comparing such rates to other samples (for example, a sample from a subject not having a relevant condition), and comparisons of sets of genomic positions with high occurrence rates of ends of cell-free DNA molecules for different tissues and/or different samples differing in a condition. A relative abundance of cell-free DNA molecules ending at the preferred ending positions relative to cell-free DNA molecules ending at other genomic positions can be compared to one or more calibration values determined from one or more calibration biological samples whose proportional contribution of the particular tissue type are known.

For determining the classification of a proportional contribution, some embodiments can use an amplitude in a fragmentation pattern. This can include the number of cell-free DNA molecules ending at a genomic position. For example, one or more local minima and one or more local maxima can be identified by analyzing the numbers of cell-free DNA molecules that end at a plurality of genomic positions. A separation value, such as a ratio, of a first number of cell-free DNA molecules at one or more local maxima and a second number of cell-free DNA molecules at one or more local minima can be shown to be positively related to a proportional contribution of the particular tissue type.

In some embodiments, a concentration of the tissue of interest can be measured in relation to the volume or weight of the cell-free DNA samples. For example, quantitative PCR can be used to measure the number of cell-free DNA molecules ending at one or more preferred ends in a unit volume or unit weight of the extracted cell-free DNA sample. Similar measurements can be made for calibration samples, and thus the proportional contribution can be determined as a proportional contribution, as the contribution is a concentration per unit volume or unit weight.

For determining a genotype of a particular tissue type (e.g., tumor tissue) in a mixture of cell-free DNA from different tissue types, some embodiments can identify a preferred ending position for the particular tissue type. For each cell-free DNA molecule of a set of cell-free DNA molecules ending on the preferred ending position, a corresponding base occurring at the preferred ending position or within the rest of the fragment can be determined. The corresponding bases can be used to determine the genotype at the preferred ending position including, for example, based on percentages of different bases seen. In various implementations, a high percentage of just one base (e.g., above 90%) can indicate the genotype is homozygous for the base, while two bases having similar percentages (e.g., between 30-70%) can lead to a determination of the genotype being heterozygous.

To identify preferred ending positions, some embodiments can compare a local maximum for left ends of cell-free DNA molecules to a local maximum for right ends of cell free DNA molecules. Preferred ending positions can be identified when corresponding local maximum are sufficiently separated. Further, amounts of cell-free DNA molecules ending on a local maximum for left/right end can be compared to an amount of cell-free DNA molecules for a local maximum with low separation to determine a proportional contribution of a tissue type.

Exemplary methods are described in PCT/US2017/058099, filed Oct. 24, 2017, which is incorporated by reference in its entirety.

D. Fragment Size

In another embodiment, an assay (e.g., first assay or a second assay) can comprise performing an assay to analyze the size of nucleic acid fragments. The assay can comprise next-generation sequencing.

The size of nucleic acids fragments derived from tumor cells can differ from those originating in non-tumor cells. In some cases, the tumor-derived DNA is shorter than the non-cancer-derived DNA in a cancer patient's plasma (Diehl F et al. Proc Natl Acad Sci USA 2005; 102: 16368-16373). Thus, the distribution of cfDNA fragment sizes can differ between samples obtained from subjects with and without cancer. Since the size of DNA fragments can be correlated to a fractional concentration (also referred to as a percentage), embodiments can use this correlation to determine a fractional concentration of a particular type of DNA, such as circulating tumor DNA, in a sample. Accordingly, methods described herein can use the fractional concentration or percentage of fragments at a particular length or a plurality of lengths to detect the presence of cancer.

The size of a cfDNA fragment can be determined using sequencing, such as massively paired end sequencing. In some embodiments, the size of a cfDNA fragment can be inferred directly from the sequencing data, such as when the paired end reads overlap or the fragment is shorter than a single read. Paired end sequence reads can also be aligned to a reference genome, such as a human genome. Exemplary tools for aligning paired end reads include the Short Oligonucleotide Alignment Program 2 (SOAP2) (soap.genomics.org.cn). The size of each sequenced fragment can be inferred from calculating the number of base pairs between the genomic coordinates corresponding to the outermost nucleotides at each end of the aligned paired end reads. A location of the nucleic acid molecule in the reference genome can be identified. The location can be any part of a genome. For example, the method can identify a chromosome from which the cfDNA fragment is derived. For each of the plurality of chromosomal regions, a respective group of nucleic acid molecules can be identified as being from a first chromosomal region based on the identified locations. The first chromosomal region can include a plurality of first loci.

A computer system can calculate a first statistical value of a size distribution of the first group of nucleic acid molecules. In embodiments, the first statistical value can be determined by computing an area under a first curve at a specified size. In some embodiments, the first curve can be a plot of a cumulative frequency of nucleic acid molecules for the first chromosomal region over a range of sizes. In some embodiments, the first statistical value can be a ratio of the number of cfDNA fragments below a threshold size to the number of cfDNA fragments above a same or different threshold size. In one embodiment, the first statistical value can be an average, mean, median, or mode of the size distribution of the fragments corresponding to the first chromosome. In another embodiment, the first statistical value can include a sum of the length of fragments below a first size, which can be a type of cutoff. For example, each of the fragments that are smaller than 200 bp can have their lengths summed. The sum can be divided by another number, such as a sum of the lengths of all fragments corresponding to the first chromosome or a sum of the lengths of fragments greater than a second size cutoff (which can be the same as the first size). For example, the first statistical value can be a ratio of the total length of fragments below a first size cutoff relative to a total length of fragments, or a ratio of the total length of small fragments relative to a total length of large fragments. Example size thresholds include 100, 110, 120, 130, 140, 150, 160, 166, 170, 180, and 190 bp in length.

The first statistical value can be compared to a first reference value, such as a control or threshold value, to determine whether the first chromosomal region exhibits an aberration.

E. Detecting Mutations Informative of Cancer

In some aspects, the methods include detecting mutations in the cfDNA that are informative of cancer in the subject. In some embodiments, the method includes detecting a mutation in a gene. In some embodiments, the method includes detecting a mutation in a plurality of genes.

In some embodiments, the methods include detecting a mutation in at least one of the group consisting of TP53, CTNNB1, AXIN1, IGF2R, SMAD2, SMAD4, RB1, CDKN2A, CCND1, p16, INK4A, IRS-1, BRCA2, p21, p15, and INK4B (see /atlasgeneticsoncology.org/Tumors/HepatoCarcinID5039.html).

In some embodiments, the method includes detecting a mutation in at least one of the group consisting of: ABCA1, BRAF, CHD5, EP300, FLT1, ITPA, MYC, PIK3R1, SKP2, TP53, ABCA7, BRCA1, CHEK1, EPHA3, FLT3, JAK1, MYCL1, PIK3R2, SLC19A1, TP73, ABCB1, BRCA2, CHEK2, EPHA5, FLT4, JAK2, MYCN, PKHD1, SLC1A6, TPM3, ABCC2, BRIP1, CLTC, EPHA6, FN1, JAK3, MYH2, PLCB1, SLC22A2, TPMT, ABCC3, BUB1B, COL1A1, EPHA7, FOS, JUN, MYH9, PLCG1, SLCO1B3, TPO, ABCC4, C1orf144, COPS5, EPHA8, FOXO1, KBTBD11, NAV3, PLCG2, SMAD2, TPR, ABCG2, CABLES1, CREB1, EPHB1, FOXO3, KDM6A, NBN, PML, SMAD3, TR10, ABL1, CACNA2D1, CREBBP, EPHB4, FOXP4, KDR, NCOA2, PMS2, SMAD4, TRRAP, ABL2, CAMKV, CRKL, EPHB6, GAB1, KIT, NEK11, PPARG, SMARCA4, TSC1, ACVR1B, CARD11, CRLF2, EPO, GATA1, KLF6, NF1, PPARGC1A, SMARCB1, TSC2, ACVR2A, CARM1, CSF1R, ERBB2, GLI1, KLHDC4, NF2, PPP1R3A, SMO, TTK, ADCY9, CAV1, CSMD3, ERBB3, GLI3, KRAS, NKX2-1, PPP2R1A, SOCS1, TYK2, AGAP2, CBFA2T3, CSNK1G2, ERBB4, GNA11, LMO2, NOS2, PPP2R1B, SOD2, TYMS, AKT1, CBL, CTNNA1, ERCC1, GNAQ, LRP1B, NOS3, PRKAA2, SOS1, UGT1A1, AKT2, CCND1, CTNNA2, ERCC2, GNAS, LRP2, NOTCH1, PRKCA, SOX10, UMPS, AKT3, CCND2, CTNNB1, ERCC3, GPR124, LRP6, NOTCH2, PRKCZ, SOX2, USP9X, ALK, CCND3, CYFIP1, ERCC4, GPR133, LTK, NOTCH3, PRKDC, SP1, VEGF, ANAPC5, CCNE1, CYLD, ERCC5, GRB2, MAN1B1, NPM1, PTCH1, SPRY2, VEGFA, APC, CD40LG, CYP19A1, ERCC6, GSK3B, MAP2K1, NQO1, PTCH2, SRC, VHL, APC2, CD44, CYP1B1, ERG, GSTP1, MAP2K2, NR3C1, PTEN, ST6GAL2, WRN, AR, CD79A, CYP2C19, ERN2, GUCY1A2, MAP2K4, NRAS, PTGS2, STAT1, WT1, ARAF, CD79B, CYP2C8, ESR1, HDAC1, MAP2K7, NRP2, PTPN11, STAT3, XPA, ARFRP1, CDC42, CYP2D6, ESR2, HDAC2, MAP3K1, NTRK1, PTPRB, STK11, XPC, ARID1A, CDC42BPB, CYP3A4, ETV4, HGF, MAPK1, NTRK2, PTPRD, SUFU, ZFY, ATM, CDC73, CYP3A5, EWSR1, HIF1A, MAPK3, NTRK3, RAD50, SULT1A1, ZNF521, ATP5A1, CDH1, DACH2, EXT1, HM13, MAPK8, OMA1, RAD51, SUZ12, ATR, CDH10, DCC, EZH2, HMGA1, MARK3, OR10R2, RAFT, TAF1, AURKA, CDH2, DCLK3, FANCA, HNF1A, MCL1, PAK3, RARA, TBX22, AURKB, CDH2O, DDB2, FANCD2, HOXA3, MDM2, PARP1, RB1, TCF12, BAI3, CDH5, DDB2, FANCE, HOXA9, MDM4, PAX5, REM1, TCF3, BAP1, CDK2, DGKB, FANCF, HRAS, MECOM, PCDH15, RET, TCF4, BARD1, CDK4, DGKZ, FAS, HSP90AA1, MEN1, PCDH18, RICTOR, TEK, BAX, CDK6, DIRAS3, FBXW7, IDH1, MET, PCNA, RIPK1, TEP1, BCL11A, CDK7, DLG3, FCGR3A, IDH2, MITF, PDGFA, ROR1, TERT, BCL2, CDK8, DLL1, FES, IFNG, MLH1, PDGFB, ROR2, TET2, BCL2A1, CDKN1A, DNMT1, FGFR1, IGF1R, MLL, PDGFRA, ROS1, TGFBR2, BCL2L1, CDKN1B, DNMT3A, FGFR2, IGF2R, MLL3, PDGFRB, RPS6KA2, THBS1, BCL2L2, CDKN2A, DNMT3B, FGFR3, IKBKE, MPL, PDZRN3, RPTOR, TNFAIP3, BCL3, CDKN2B, DOT1L, FGFR4, IKZF1, MRE11A, PHLPP2, RSPO2, TNKS, BCL6, CDKN2C, DPYD, FH, IL2RG, MSH2, PIK3C3, RSPO3, TNKS2, BCR, CDKN2D, E2F1, FHOD3, INHBA, MSH6, PIK3CA, RUNX1, TNNI3K, BIRC5, CDX2, EED, FIGF, INSR, MTHFR, PIK3CB, SDHB, TNR, BIRC6, CEBPA, EGF, FLG2, IRS1, MTOR, PIK3CD, SF3B1, TOP1, BLM, CERK, EGFR, FLNC, IRS2, MUTYH, PIK3CG, SHC1, and TOP2A.

III. POSITIVE PREDICTIVE VALUE

Provided herein are methods of detecting or assessing a disease or condition using a combination of assays that provides a positive predictive value that can be greater than the positive predictive value for detecting or assessing the condition based on a first assay alone. Assays of the present disclosure can be used to generate a positive or negative outcome based on the results of the assay. This outcome can be used to suggest the presence or absence of a condition (e.g., cancer) in a subject. In some embodiments, the cancer is HCC.

A positive predictive value can correspond to a ratio of subjects who are actually positive for a condition (true positives) to subjects identified as having the condition (true positives+false positives). In particular, methods of the present disclosure can include performing a first assay with a high sensitivity, followed by a second, high specificity assay for those samples that are positive in the first assay, thereby increasing the positive predictive value of the overall screen.

The methods can also include combining a first assay that is lower in cost or easier to perform with a second assay that is higher in cost or harder to perform. Thus, the test can use the first assay to determine if the second assay is necessary.

Thus, the present disclosure provides methods for assessing a condition in a subject. Exemplary conditions include cancer and liver conditions, including liver cancers. In some cases, the liver cancer is hepatocellular carcinoma. Assessing a condition can comprise performing one or more assays to identify the presence of the condition. In particular, methods of the present disclosure can include performing a first assay to analyze a first biological sample and a second assay to analyze a second biological sample. In some cases, the biological samples can be the same biological sample. For example, the biological samples can be two or more aliquots of the same blood draw or plasma sample. In other cases, the biological samples can be different. For example, the biological samples can be two different plasma samples obtained at different times. Both a first and second assay can be performed on samples obtained using noninvasive methods, thereby minimizing the need for unnecessary invasive testing. Examples of noninvasive methods include the collection of blood, serum, or plasma.

The first and second assays can comprise the same assay or analysis, but can be performed using different read depths. For example, the first assay can comprise sequencing nucleic acids at a lower read depth than the second assay. A shallow read depth can be about 20 million, about 40 million, about 60 million, about 80 million, or about 100 million reads. A shallow read depth can correspond to about 1 fold coverage (1×), about 1.5 fold coverage (1.5×), about 2 fold coverage (2×), about 3 fold coverage (3×), about 4 fold coverage (4×), about 5 fold coverage (5×), or about 10 fold coverage (10×). In some embodiments, about 20 million reads corresponds to about 1 fold coverage. In some embodiments, the first assay is performed using a shallow read depth, such as 30 million reads, and the second assay is performed at a deeper read depth, such as more than 100 million sequencing reads, including 150, 200, 25, 300, 350, 400, 450, 500, 600, 700, 800, or 900 million sequencing reads or more. In some aspects, deep sequencing can comprise 1, 2, 3, 4, or 5 billion sequencing reads or more.

The first and second assays can comprise the different assays or analysis that can be performed using different read depths. For example, the first assay can comprise sequencing nucleic acids at a lower read depth than the second assay. A shallow read depth can be about 20 million, about 40 million, about 60 million, about 80 million, or about 100 million reads. A shallow read depth can correspond to about 1 fold coverage (1×), about 1.5 fold coverage (1.5×), about 2 fold coverage (2×), about 3 fold coverage (3×), about 4 fold coverage (4×), about 5 fold coverage (5×), or about 10 fold coverage (10×). The second assay can be performed using a higher read depth than the first assay. A higher read depth can correspond to about 10 fold coverage (10×), about 1000 fold coverage (1000×), about 10,000 fold (10,000×), or about 30,000 fold coverage (30,000×). A higher read depth can correspond to greater than 10 fold coverage. In some embodiments, about 20 million reads corresponds to about 1 fold coverage. In some embodiments, the first assay is performed using a shallow read depth, such as 30 million reads, and the second assay is performed at a deeper read depth, such as more than 100 million sequencing reads, including 150, 200, 25, 300, 350, 400, 450, 500, 600, 700, 800, or 900 million sequencing reads or more. In some aspects, deep sequencing can comprise 1, 2, 3, 4, or 5 billion sequencing reads or more.

In one embodiment, the first assay is performed using a shallow read depth, such as 5×, and the second assay is performed at a read depth of 10×. In one embodiment, the first assay is performed using a shallow read depth, such as 5×, and the second assay is performed at a read depth of greater than 10,000×. In one embodiment, the first assay is performed using a shallow read depth, such as 2×, and the second assay is performed at a read depth of greater than 5×. In one embodiment, the first assay is performed using a shallow read depth, such as 2×, and the second assay is performed at a read depth of greater than 10,000×. In one embodiment, the first assay is performed using a shallow read depth, such as less than 10×, and the second assay is performed at a read depth of greater than 10×.

In some embodiments, the depth of sequencing reads of an assay (e.g., the first assay or the second assay) can be based on a characteristic of the individual. For example, the characteristic could be a characteristic associated with a disease, such as a family history of the disease, a prior positive test for the disease, or at least one risk factor for the disease. In one example, the presence of the characteristic associated with the disease could require the sequencing depth being higher than the sequencing depth used if the individual did not have the characteristic associated with the disease. In another example, the presence of the characteristic associated with the disease could result in the depth of sequencing being lower than the depth of sequencing used if the individual did not have the characteristic associated with the disease. For example, a low depth screening test for lung or liver cancer can be recommended for low risk populations; and vice versa.

In some embodiments, the methods described herein comprise determining a baseline copy number. The baseline copy number can be determined from sequencing data from a control. The control can be a normal individual, wherein the normal individual does not suffer from a condition. The control can be obtained by analyzing sequencing data from a plurality of normal individuals, wherein the normal individuals do not suffer from a condition. The sequencing data from the control can be at a shallow read depth. A shallow read depth can be about 20 million, about 40 million, about 60 million, about 80 million, or about 100 million reads. A shallow read depth can correspond to about 1 fold coverage (1×), about 1.5 fold coverage (1.5×), about 2 fold coverage (2×), about 3 fold coverage (3×), about 4 fold coverage (4×), about 5 fold coverage (5×), or about 10 fold coverage (10×). In some embodiments, determining the baseline comprises obtaining sequencing data from the plurality of normal individuals at a read depth greater than the read depth of the first assay. For example, the read depth for determining the baseline can be 5× while the read depth of the first assay can be 2×. The baseline can be indicative of the copy number in individuals who do not suffer from the condition. A threshold can be the baseline copy number. The threshold can be a distance from the baseline copy number. The distance from the baseline can be a standard deviation from the baseline copy number. The standard deviation can be 1, 2, 3, 4, or 5 standard deviations from the baseline copy number. The threshold can be used to identify a copy number variation in an individual suffering from a condition. The copy number variation can be a copy number gain or a copy number loss relative to the baseline copy number. An individual with a copy number variation above the threshold can determined to have a copy number variation. In some cases, the second assay is only performed if the first assay is above or below the threshold.

The second assay can comprise sequencing a genome of the individual or a targeted region of the genome of the individual. Sequencing the genome of the individual can comprise whole genome sequencing (WGS). The targeted region of the genome can be a region of the genome associated with a disease. The targeted region of the genome can be a region of the genome where a copy number variation was detected in the first assay. The targeted region can be a chromosome, a locus, or a set of loci. In some instances, the PPV of the second assay is greater than the PPV of the first assay. In some instances, the PPV of a combination of the first assay and the second assay is greater than the PPV first assay.

In some embodiments, methods of the present disclosure comprise performing two assays or more assays (e.g., a first assay and a second assay). The second assay can be performed to improve the sensitivity, specificity, negative predictive value and/or positive predictive value of the first assay or overall method. In some embodiments, methods of the present disclosure comprise performing an assay (e.g., a first assay and/or a second assay) having a sensitivity and/or specificity for a marker or set of markers indicative of a tumor. The sensitivity of an assay can refer to the number of true positives divided by the sum of the number of true positives and false negatives. Sensitivity can characterize the ability of an assay or method to correctly identify a proportion of the population that truly has a condition. In some embodiments, an assay can have a sensitivity of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% for a set of markers indicative of a tumor.

For example, a method of the present disclosure can comprise a first assay, and the first assay can have a sensitivity for a first set of markers indicative of a tumor of at least about 80%. In some embodiments, the sensitivity of an assay can be within a range (e.g., between about 75% and about 85%, between about 65% and about 95%, between about 60% and about 100%, between about 10% and about 25%, between about 90% and about 100%).

Alternatively, a first assay can have a sensitivity or PPV that is lower than that of an overall test (e.g., one that involves the use of more than one assay).

In one example, a first assay in a method has a sensitivity of up to 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%.

In some embodiments, a method of the present disclosure can comprise one or more assays, and the method can have a sensitivity of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (e.g., for detecting a tumor in a subject). Thus, the combined sensitivity of two or more assays can result in any of the above sensitivities.

For example, a method for screening cancer can involve performing a first assay to screen for individuals who have cancer, the true positives (TP). The screen can capture more false positives (FP) (individuals that do not have cancer) than would otherwise be desired. This can result in a low positive predictive value (PPV). However, a second assay performed on the same or new samples from the TP and FP individuals that has a lower false positive rate, can increase the PPV of the overall test.

The specificity of an assay can refer to the number of true negatives divided by the sum of the number of true negatives and false positives. Specificity can characterize the ability of an assay or method to correctly identify a proportion of the population that truly does not have a condition.

In some embodiments, an assay can have a specificity of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% for a set of markers indicative of a tumor.

For example, a method of the present disclosure can comprise a first assay, and the first assay can have a specificity for a marker or first set of markers indicative of a tumor of at least about 80%. In some embodiments, the specificity of an assay can be within a range (e.g., between about 75% and about 85%, between about 65% and about 95%, between about 60% and about 100%, between about 10% and about 25%, between about 90% and about 100%).

In one example, a first assay in a method has a specificity of up to 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, a method of the present disclosure can comprise one or more assays, and the method can have a specificity of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (e.g., for detecting that a subject does not have a tumor). Thus, the combined sensitivity of two or more assays can result in any of the above sensitivities.

The negative predictive value of an assay can refer to the probability that subjects with a negative screening test truly don't have the disease, and can be inherently impacted by the prevalence of a condition in a population.

In some embodiments, an assay can have a negative predictive value of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In a particular example, a method of the present disclosure can comprise a second assay, and the second assay can have a negative predictive value of at least about 70%. In some embodiments, the negative predictive value of an assay can fall within a range (e.g., between about 65% and about 75%, between about 55% and about 65%, between about 60% and about 100%, between about 10% and about 25%, between about 90% and about 100%).

In one example, an assay, such as a first assay has a negative predictive value that is up to %, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, a method of the present disclosure can comprise one or more assays, and the method can have a negative predictive value of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (e.g., for detecting that a subject does not have a tumor).

In some embodiments, the negative predictive value of a method can fall within a range (e.g., between about 80% and about 90%, between about 90% and about 100%, between about 70% and about 80%, between about 10% and about 25%, between about 25% and about 50%).

The positive predictive value of an assay can refer to the probability that subjects with a positive screening test truly have the disease, and it can be inherently impacted by the prevalence of a condition in a population.

In some embodiments, an assay can have a positive predictive value of at least, or at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In a particular example, a method of the present disclosure can comprise a second assay, and the second assay can have a positive predictive value of at least about 70%.

In some embodiments, an assay (e.g., a first assay) can have a positive predictive value of at most about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. After the first assay is performed, one or more additional assays can be performed on the positives (true positives and false positives) to increase the overall positive predictive value of the test. The increase in PPV is preferably at least 2 fold, 3 fold, 4 fold, 5 fold, 7.5 fold, 10 fold, or 20 fold. The increase in PPV can be about 4 fold to about 10 fold, about 5 fold to about 10 fold, or about 5 fold to about 15 fold, or about 5 fold to about 20 fold.

For example, a first assay can have a positive predictive value of at most about 4%, whereas a second assay can have a positive predictive value of at least about 11%. In some embodiments, the positive predictive value of an assay can fall within a range (e.g., between about 65% and about 75%, between about 90% and about 100%, between about 70% and about 80%, between about 10% and about 25%, between about 25% and about 50%). For example, a first assay can have a positive predictive value of between about 3% and 5%, whereas a second assay can have a positive predictive value of between about 10% and 15%.

In some embodiments, a method of the present disclosure can comprise one or more assays, and the overall method can have a positive predictive value of at least about 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (e.g., for detecting that a subject does not have a tumor).

In some embodiments, the positive predictive value of the overall method can fall within a range (e.g., between about 15% and about 30%, about 20% and about 40%, about 20% and about 50%, about 30% and about 50%, about 50% and about 70%, about 60% and about 70%, about 80% and about 90%, between about 90% and about 100%, between about 70% and about 80%, between about 10% and about 25%, between about 25% and about 50%).

Where the method comprises a first assay and a second assay, the positive predictive value of the second assay can be at least, or at least about 1.1-fold, 1.2-fold, 1.3-fold, 1.4-fold, 1.5-fold, 2-fold, 2.5-fold, 3-fold, 3.5-fold, 4-fold, 4.5-fold, 5-fold, 6-fold, 7-fold, 8-fold, 9-fold, 10-fold, 15-fold, 20-fold, 25-fold, 30-fold, 35-fold, 40-fold, 45-fold, 50-fold, 75-fold, 100-fold, or more than 100-fold greater than the positive predictive value of the first assay. Alternatively, or in addition to, the positive predictive value of the overall method (e.g., two or more assays) can be at least 1.1-fold, 1.2-fold, 1.3-fold, 1.4-fold, 1.5-fold, 2-fold, 2.5-fold, 3-fold, 3.5-fold, 4-fold, 4.5-fold, 5-fold, 6-fold, 7-fold, 7.5-fold, 8-fold, 9-fold, 10-fold, 15-fold, 20-fold, 25-fold, 30-fold, 35-fold, 40-fold, 45-fold, 50-fold, 75-fold, 100-fold, greater than the positive predictive value of the first assay, or a single assay of the method, alone.

For example, the positive predictive value of the second assay can be 4-fold greater than the positive predictive value of the first assay. In some embodiments, the positive predictive value of the second assay can greater than the positive predictive value of the first assay, and the value for the fold-change in positive predictive value can fall within a range. For example, the positive predictive value of the second assay can be about 2-fold to 6-fold greater than the positive predictive value of the first assay. In another example, the positive predictive value of the second assay can be about 3.8-fold to about 4.2 fold greater than the positive predictive value of the first assay.

An screen or an assay can have a false positive rate, which can be about, or less than 01.%, 0.25%, 0.5%, 0.75%, 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Performing one or more additional assays can reduce the false positive rate for an overall screen or method about, or at least 1.1-fold, 1.2-fold, 1.3-fold, 1.4-fold, 1.5-fold, 2-fold, 2.5-fold, 3-fold, 3.5-fold, 4-fold, 4.5-fold, 5-fold, 6-fold, 7-fold, 7.5-fold, 8-fold, 9-fold, 10-fold, 13-fold, 15-fold, 20-fold, 25-fold, 30-fold, 35-fold, 40-fold, 45-fold, 50-fold, 75-fold, or 100-fold. The false positive rate for an overall screen or method involving two more assays (e.g., 2, 3, 4, 5, 6, 7, 8, 9, or 10 assays) can be about, or less than 01.%, 0.2%, 0.25%, 0.3%, 0.4%, 0.5%, 0.6%, 0.7%, 0.75%, 0.8%, 0.9%, 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Positive and negative likelihood ratios (LR+ and LR−, respectively) can quantify the change in the certainty of the "diagnosis" conferred by test results. More specifically, the likelihood ratios can transform the pretest odds to the posttest odds of a given (positive or negative) diagnosis. A high positive likelihood ratio and/or a low negative likelihood ratio can describe an assay or method of the present disclosure having a very good ability to predict the true disease status of a subject. A completely non-informative assay can have positive and negative likelihood ratios equal to 1 (i.e., does not transform the pre-test odds substantially). In some instances, a positive likelihood ratio of 10 or more and a negative likelihood ratio of 0.1 or less can represent informative tests. In some embodiments, the positive likelihood ratio of an assay or method of the present disclosure can be at least about 0.1, 0.5, 1, 2, 3, 4, 5, 6, 7, 8, 9, or 10. In some embodiments, the positive likelihood ratio of an assay or method can fall within a range (e.g., between about 5 and about 8). In some embodiments, the negative likelihood ratio of an assay or method of the present disclosure can be at most about 10, 9, 8, 7, 6, 5, 4, 3, 2, 1, 0.5, or 0.1. In some embodiments, the negative likelihood ratio of an assay or method can fall within a range (e.g., between about 0.1 and about 0.5).

IV. SEQUENCING

The methods described herein can comprise sequencing nucleic acid (e.g., cell-free nucleic acid) from a sample. Sequencing can comprise whole genome sequencing. Sequencing can comprise random or targeted sequencing. Sequencing can be performed so as to enable analysis of a methylation status of cell-free nucleic acid. In some cases, sequencing is bisulfite sequencing.

Sequencing can comprise deep sequencing. Deep sequencing can comprise more than 100 million sequencing reads, including 150, 200, 25, 300, 350, 400, 450, 500, 600, 700, 800, or 900 million sequencing reads or more. In some aspects, deep sequencing can comprise 1, 2, 3, 4, or 5 billion sequencing reads or more. Sequencing can comprise shallow sequencing. Shallow sequencing can comprise generating less than 100, 90, 80, 70, 60, 50, 40, 30, 20, or 10 million sequencing reads. Shallow sequencing can be useful in eliminating undesired sequencing reads from a sample which comprises an abundance of a desired nucleic acid type. For example, shallow sequencing can be useful in obtaining sequencing reads from nucleic acid derived from liver tissue when obtained from a plasma sample by minimizing sequencing reads obtained from nucleic acid that is not derived from liver tissue.

Sequencing can be used to generate one or more sequencing reads. A sequencing read or sequence read can refer to sequence information corresponding to a nucleic acid molecule. A sequencing read can correspond to a series of nucleotides (e.g., about 20 to about 150) from a nucleic acid fragment. A sequencing read can correspond to nucleotides of an entire nucleic acid fragment. Sequencing reads can be obtained by a variety of methods. Sequencing reads can be obtained using nucleic acid amplification (e.g., polymerase chain reaction, linear amplification, isothermal amplification). Amplification can comprise whole genome amplification. Amplification can comprise targeted amplification. Alternatively, sequencing reads can be obtained without the use of amplification (i.e., nucleic acid can be sequenced directly). Direct sequencing of nucleic acid (e.g., nucleic acid obtained from a biological sample), can be useful in improving the accuracy of analysis. For example, direct sequencing of nucleic acid obtained from a biological sample can improve accuracy of copy number aberration analysis by minimizing skewing.

The cell-free nucleic acids can be from a targeted region of the genome. The targeted region of the genome can be a chromosome, a locus, or a set of loci. Obtaining the cell-free nucleic acids from the targeted genomic region of the genome can comprise enrichment using a targeted method. The methods described herein can comprise enriching the cell-free nucleic acid from the targeted region prior to sequencing. Enrichment can comprise the use of hybridization probes to capture the cell-free nucleic acid.

The nucleic acid molecules, e.g., cell-free nucleic acid molecules, can be enriched by a targeted method. The number of nucleic acid molecule targets that can be enriched can be about 1, about 10, about 100, about 1000, about 10,000, about 100,000, about 1,000,000, or about 10,00,000. The number of nucleic acid molecule targets that can enriched can be greater than 1, greater than 10, greater than 100, greater than 1000, greater than 10,000, greater than 100,000, greater than 1,000,000, or greater than 10,000,000. Targets that are enriched can be used for downstream applications, e.g., sequencing, e.g., next-generation sequencing.

The one or more targets can be enriched using one or more capture probes, e.g., using SURESELECT Target Enrichment from AGILENT TECHNOLOGIES. Nucleic acid, e.g., DNA, e.g., genomic DNA, can be fragmented, e.g., by sonication. The one or more targets can be enriched using one or more probes, e.g., one or more cRNA probes, of about 10 to about 200 bases, about 20 to about 175 bases, about 25 to about 150 bases, or about 120 bases. The one or more probes, e.g., one or more cRNA probes, can be labeled with a label, e.g., biotin, and the label can be bound to a solid support, e.g., a bead (e.g., a magnetic bead), e.g., through a binding moiety, e.g., streptavidin. The solid support, e.g., beads, e.g., magnetic beads, can be captured, e.g., using a magnet. The one or more captured targets can be unbound from the solid support (e.g., by digesting the cRNA probes) amplified, e.g., by PCR, and analyzed, e.g., by sequencing, e.g., next-generation sequencing.

The one or more targets can be enriched, e.g., using HALOPLEX Target Enrichment System from AGILIENT TECHNOLOGIES. Nucleic acid, e.g., DNA, e.g., genomic DNA, can be fragmented, e.g., by restriction enzyme digestion. A probe in the presence of an indexing primer cassette can be used to generate a DNA fragment that is circularized and has one or more indexes incorporated and optionally has one or more sequencing motifs useful for a sequencing platform, e.g., Illumina sequencing. The probe can comprise a label, e.g., biotin, that can be added, e.g., by biotinylation. The label probe can be captured, e.g., using a streptavidin-coated bead (e.g., a magnetic bead). Captured targets can be amplified, e.g., by PCR, and analyzed, e.g., by sequencing, e.g., next-generation sequencing.

The one or more targets can be enriched, e.g., using a transposase, e.g., using NEXTERA tagmentation. The one or more targets can be enriched by addition of adaptors through transposition and then amplifying using primers that anneal to the adaptors by PCR.

The one or more targets can be enriched, e.g., using SEQCAP from ROCHE. Nucleic acid, e.g., DNA, e.g., genomic DNA, can be fragmented, e.g., by sonication. The fragmented DNA can be annealed to capture probes. The capture probes can be labeled. The probes can be bound to solid supports, e.g., magnetic beads coated with streptavidin. The captured targets can be released, amplified, and sequenced.

The one or more targets can be enriched using Single Primer Enrichment Technology (SPET) from NUGEN. Adaptors can be attached to nucleic acid fragments. Primers comprising 3' adaptors can be annealed to target sequence and extended. The extended products can be amplified using primers to adaptor sequences and the amplified products can be analyzed by sequencing, e.g., next-generation sequencing.

V. SAMPLES

The methods of the present disclosure can relate to detecting a cancer or a tumor in a subject. The subject can be any human patient, such as a cancer patient, a patient at risk for cancer, or a patient with a family or personal history of cancer. In some cases, the subject is in a particular stage of cancer treatment. In some cases, the subject can have or be suspected of having cancer. In some cases, the subject is asymptomatic to cancer. In some cases, whether the subject has cancer is unknown.

Where relevant in the description herein, a subject can have any type of cancer or tumor. In some embodiments, the subject can have or can be suspected of having hepatocellular carcinoma (HCC). In some embodiments, a subject can have nasopharyngeal cancer, or cancer of the nasal cavity. In another example, a subject can have oropharyngeal cancer, or cancer of the oral cavity. Non-limiting examples of cancer can include adrenal cancer, anal cancer, basal cell carcinoma, bile duct cancer, bladder cancer, cancer of the blood, bone cancer, a brain tumor, breast cancer, bronchus cancer, cancer of the cardiovascular system, cervical cancer, colon cancer, colorectal cancer, cancer of the digestive system, cancer of the endocrine system, endometrial cancer, esophageal cancer, eye cancer, gallbladder cancer, a gastrointestinal tumor, hepatocellular carcinoma, kidney cancer, hematopoietic malignancy, laryngeal cancer, leukemia, liver cancer, lung cancer, lymphoma, melanoma, mesothelioma, cancer of the muscular system, Myelodysplastic Syndrome (MDS), myeloma, nasal cavity cancer, nasopharyngeal cancer, cancer of the nervous system, cancer of the lymphatic system, oral cancer, oropharyngeal cancer, osteosarcoma, ovarian cancer, pancreatic cancer, penile cancer, pituitary tumors, prostate cancer, rectal cancer, renal pelvis cancer, cancer of the reproductive system, cancer of the respiratory system, sarcoma, salivary gland cancer, skeletal system cancer, skin cancer, small intestine cancer, stomach cancer, testicular cancer, throat cancer, thymus cancer, thyroid cancer, a tumor, cancer of the urinary system, uterine cancer, vaginal cancer, or vulvar cancer. The term 'lymphoma' can refer to any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The term 'leukemia' can refer to any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia. In some cases, the cancer patient does not have a particular type of cancer. For example, in some instances, a patient can have a cancer that is not breast cancer.

Examples of cancer include cancers that cause solid tumors as well as cancers that do not cause solid tumors. Furthermore, any of the cancers mentioned herein can be a primary cancer (e.g., a cancer that is named after the part of the body where it first started to grow) or a secondary or metastatic cancer (e.g., a cancer that has originated from another part of the body).

A subject at risk of cancer can be at risk because of a particular condition such as a precancerous condition. Precancerous conditions include but are not limited to actinic keratosis, Barrett's esophagus, atrophic gastritis, ductal carcinoma in situ, dyskeratosis congenita, sideropenic dysphagia, lichen planus, oral submucous fibrosis, solar elastosis, cervical dysplasia, leukoplakia, and erythroplakia). In some cases, a patient can be at risk of cancer because of cell or tissue dysplasia (e.g., an abnormal change in cell number, abnormal change in cell shape, abnormal change in cell size, or abnormal change in cell pigmentation). A subject that is at risk of cancer can be a patient that was exposed to a carcinogenic agent. Such patients can include patients with exposure to known or probable carcinogens (e.g., acetyl aldehyde, asbestos, or tobacco products), or patients exposed to ionizing radiation (e.g., gamma radiation, beta-radiation, X-radiation, or ultraviolet radiation). In some cases, a patient at risk of cancer is at risk because of a family history of cancer.

In some embodiments, a method of the present disclosure can detect a tumor or cancer in a subject, wherein the tumor or cancer has a geographic pattern of disease. In one example, the subject can have hepatitis, including hepatitis caused by hepatitis A, hepatitis B, or hepatitis C. In some cases, the subject has HCC associated with hepatitis. In some cases, the subject has HCC associated with HBV or HCV. In another example, a subject can have an EBV-related cancer (e.g., nasopharyngeal cancer), which can be prevalent in South China (e.g., Hong Kong SAR). In another example, subject can have an HPV-related cancer (e.g., oropharyngeal cancer), which can be prevalent in the United States and Western Europe. In yet another example, a subject can have a Human T-lymphotrophic virus-1 (HTLV-1)-related cancer (e.g., adult T-cell leukemia/lymphoma), which can be prevalent in southern Japan, the Caribbean, central Africa, parts of South America, and in some immigrant groups in the southeastern United States.

Both DNA and RNA viruses have been shown to be capable of causing cancer in humans. In some embodiments, a subject can have a cancer caused by a virus (e.g., an oncovirus). In some embodiments, a subject can have a cancer, and the cancer can be detectable using viral DNA. In some embodiments, a subject can have cancer, and the cancer can be detectable using tumor-derived viral DNA. In some embodiments, a subject can have a cancer, and the cancer can be detectable using tumor-derived viral DNA, or a fragment thereof, in cell-free sample obtained from the subject (e.g., a blood sample, a plasma sample, or a serum sample). A person having skill in the art will appreciate that a virus can have multiple viral strains (e.g., related viruses that can differ in their genetic makeup). For example, a subject can have oral, oropharyngeal, cervical cancer, penile, anal, vaginal, or vulvar cancer caused by (or associated with) infection by a Human papilloma virus (HPV), which can include more than 150 related viruses. Infection with the Epstein-Barr virus (EBV) can also increase a subject's risk of developing nasal cancer, nasopharyngeal cancer, lymphomas (e.g., Burkitt lymphoma or Hodgkin lymphoma), or stomach cancer. In yet another example, infection with the Hepatitis B virus (HBV) or Hepatitis C virus can cause chronic infections, which can increase a subject's chance of developing liver cancer. Non-limiting examples of viruses that can cause, or be associated with, cancer in a subject include HPV, EBV, HBV, HCV, Human immunodeficiency virus (e.g., associated with Kaposi sarcoma, cervical cancer, non-Hodgkin lymphoma, anal cancer, Hodgkin disease, lung cancer, oral cancer, oropharyngeal cancer, skin cancer, and liver cancer), human herpes virus 8 (e.g., associated with Kaposi sarcoma, blood cancer, primary effusion lymphoma, and Castleman disease), Human T-lymphotrophic virus-1 (e.g., associated with lymphocytic leukemia, non-Hodgkin lymphoma, and adult T-cell leukemia/lymphoma), and Merkel cell polyomavirus (e.g., associated with skin cancers such as Merkel cell carcinoma). In some embodiments, a non-human subject (e.g., a primate) can have cancer, and the cancer can be detectable using tumor-derived viral DNA. For example, infection with Simian virus 40 (SV40) can increase a subject's risk of developing mesothelioma, brain tumor, bone cancer, and lymphoma.

A subject from whom a sample is taken, or is treated by any of the methods or compositions described herein can be of any age and can be an adult, infant or child. In some cases, the subject, e.g., patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between about 2 and about 20 years old, between about 20 and about 40 years old, or between about 40 and about 90 years old). A particular class of subjects, e.g., patients that can benefit from a method of the present disclosure is subjects, e.g., patients over the age of 40. Another particular class of subjects, e.g., patients that can benefit from a method of the present disclosure is pediatric patients, who can be at higher risk of chronic heart symptoms. Furthermore, a subject, e.g., patient from whom a sample is taken, or is treated by any of the methods or compositions described herein, can be male or female.

Any of the methods disclosed herein can also be performed on a non-human subject, such as a laboratory or farm animal, or a cellular sample derived from an organism disclosed herein. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, a cow, or a zebrafish. A sample can be obtained from a subject invasively (e.g., surgical means) or non-invasively (e.g., a blood draw, a swab, or collection of a discharged sample).

VI. ENUMERATED EMBODIMENTS

1. A method of screening for a condition of a subject, the method comprising: performing a first assay comprising: obtaining a first plurality of sequencing reads at a first read depth from a first sample comprising cell-free nucleic acids obtained from the subject, analyzing the first plurality of sequencing reads for a copy number aberration; and detecting a presence of the copy number aberration in the first plurality of sequencing reads; conditionally performing a second assay upon the detection of the copy number aberration in the first plurality of sequencing reads, the second assay comprising: obtaining a second plurality of sequencing reads at a second read depth from a second sample comprising cell-free nucleic acids obtained from the subject; analyzing the second plurality of sequencing reads for a biomarker of the condition of the subject, thereby screening the subject for the condition based on detecting the biomarker in the second plurality of sequencing reads, wherein the second plurality of sequencing reads comprises a greater read depth than the first plurality of sequencing reads and wherein a positive predictive value of screening the subject for the condition based on the second assay is greater than a positive predictive value of screening the subject for the condition based on the first assay alone.

2. The method of embodiment 1, wherein the first plurality of sequencing reads comprises sequencing reads from a whole genome survey. 3. The method of embodiment 1 or embodiment 2, wherein the first plurality of sequencing reads comprises sequencing reads informative of a methylation profile of the cell-free nucleic acids in the first sample. 4. The method of any one of embodiments 1-3, wherein the read depth of the first plurality of sequencing reads is 10× or less, 5× or less, 4× or less, 3× or less, or 2× or less. 5. The method of any one of embodiments 1-4, wherein the read depth of the second plurality of sequencing reads is 5× or less, 10× or less, 20× or less, 50× or less, 100× or less, 250× or less, 500× or less, 1,000× or less, 2,500× or less, 5,000× or less, 10,000× or less, 15,000× or less, 20,000× or less, 30,000× or less, 40,000× or less, 50,000× or less, 75,000× or less, 100,000× or less, or 250,000× or less. 6. The method of any one of embodiments 1-5, wherein the first plurality of sequencing reads comprises 200 million reads or less, 100 million reads or less, 80 million reads or less, 60 million reads or less, or 40 million reads or less. 7. The method of any one of embodiments 1-6, wherein the second plurality of sequencing reads comprises 100 million reads or more, 200 million reads or more, 400 million reads or more, 1 billion reads or more, 2 billion reads or more, 5 billion reads or more, 10 billion reads or more, 20 billion reads or more, or 50 billion reads or more. 8. The method of any one of embodiments 1-7, wherein the second plurality of sequencing reads comprises sequencing reads from a whole genome survey. 9. The method of embodiment 1-7, wherein the second plurality of sequencing reads comprises sequencing reads from a targeted region of a genome, wherein the targeted region of the genome comprises a subset of chromosomes, a single chromosome, a subset of genomic loci, or a single genomic locus. 10. The method of any one of embodiments 1-9, wherein detecting the presence of the copy number aberration in the first plurality of sequencing reads comprises comparing an amount of the first plurality of sequencing reads originating from a first chromosomal region to a cutoff value. 11. The method of any one of embodiments 10, wherein detecting the presence of the copy number aberration in the first plurality of sequencing reads comprises detecting an absolute number of sequencing reads identified as originating from the first chromosomal region. 12. The method of any one of embodiments 1-11, wherein detecting the presence of the copy number aberration in the first plurality of sequencing reads comprises detecting the copy number aberration originating from a first tissue of interest. 13. The method of embodiment 12, wherein the tissue of interest is a liver tissue, a lung tissue, a pancreatic tissue, a stomach tissue, a brain tissue, a cardiac tissue, a muscle, a kidney tissue, a red blood cell, or a skin tissue. 14. The method of any one of embodiments 10-13, wherein the biomarker of the condition comprises a presence of the copy number aberration in the second plurality of sequencing reads, and wherein the second assay comprises comparing an amount of the second plurality of sequencing reads originating from the first chromosomal region to a cutoff value. 15. The method of any one of embodiments 14, wherein detecting the presence of the copy number aberration in the second plurality of sequencing reads comprises comparing an amount of the second plurality of sequencing reads originating from a second chromosomal region to a cutoff value. 16. The method of any one of embodiments 14-15, wherein detecting the presence of the copy number aberration in the second plurality of sequencing reads comprises detecting an absolute number of sequencing reads identified as originating from the first chromosomal region. 17. The method of any one of embodiments 14-16, wherein detecting the presence of the copy number aberration in the second plurality of sequencing reads comprises detecting an absolute number of sequencing reads identified as originating from the second chromosomal region. 18. The method of any one of embodiment 14-17, wherein detecting the presence of the copy number aberration in the second plurality of sequencing reads comprises detecting a copy number aberration originating from the first tissue of interest. 19. The method of any one of embodiment 14-17, wherein detecting the presence of the copy number aberration in the second plurality of sequencing reads comprises detecting a copy number aberration originating from a second tissue of interest. 20. The method of embodiment 19, wherein the second tissue of interest is a liver tissue. 21. The method of embodiment 19, wherein the first tissue of interest and the second tissue of interest are the same. 22. The method of any one of embodiments 1-21, further comprising obtaining the first sample comprising cell-free nucleic acids from the subject. 23. The method of any one of embodiments 1-22, further comprising sequencing the cell-free nucleic acids in the first sample to obtain the first plurality of sequencing reads at the first read depth. 24. The method of any one of embodiments 1-23, further comprising obtaining the second sample comprising cell-free nucleic acids from the subject. 25. The method of any one of embodiments 1-24, further comprising sequencing the cell-free nucleic acids in the second sample to obtain the second plurality of sequencing reads at the second read depth. 26. The method of any one of embodiments 22-25, wherein the first sample and the second sample are obtained from the subject at the same time. 27. The method of any one of embodiments 22-26, wherein the first sample and the second sample are each a subsample of a single blood draw from the subject. 28. The method of any one of embodiments 1-27, the second assay is performed within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after performing the first assay. 29. The method of embodiment 28, wherein the second sample is cryogenically preserved for 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after performing the first assay. 30. The method of any one of embodiments 1-29, wherein the condition is a liver condition. 31. The method of embodiment 30, wherein the liver condition is selected from the group consisting of liver cirrhosis, hepatocellular carcinoma, nonalcoholic fatty liver disease, nonalcoholic steatohepatitis, and a combination thereof. 32. The method of any one of embodiments 1-31, wherein the at least a subset of the first plurality of cell-free nucleic acids and the at least a subset of the second plurality of cell-free nucleic acids comprise cell-free nucleic acids that are from a hepatocellular carcinoma. 33. The method of any one of embodiments 1-32, wherein the copy number aberration comprises a duplication or a deletion of a genomic locus. 34. The method of any one of embodiments 1-33, wherein the second assay comprises determining that a subset of the second plurality of cell-free nucleic acids is from a liver tissue. 35. The method of any one of embodiments 1-34, wherein the condition is a cancer type, and wherein the second assay is used to determine the cancer type. 36. The method of any one of embodiments 1-35, wherein the cancer type is hepatocellular carcinoma. 37. The method of any one of embodiments 1-36, wherein the first plurality of cell-free nucleic acids and the second plurality of cell-free nucleic acids are from one or more plasma samples. 38. The method of any one of embodiments 1-37, wherein the first plurality of cell-free nucleic acids comprises deoxyribonucleic acids. 39. The method of any one of embodiments 1-38, wherein the first plurality of cell-free nucleic acids comprises ribonucleic acids. 40. The method of any one of embodiments 1-39, wherein the second plurality of cell-free nucleic acids comprises deoxyribonucleic acids. 41. The method of any one of embodiments 1-40, wherein the second plurality of cell-free nucleic acids comprises ribonucleic acids. 42. The method of any one of embodiments 23-41, wherein the first assay comprises an amplification of the first plurality of cell-free nucleic acids before the sequencing. 43. The method of any one of embodiments 42, wherein the amplification comprises a whole genome amplification or a targeted amplification. 44. The method of any one of embodiments 23-41, wherein the first plurality of cell-free nucleic acids are not amplified before the sequencing. 45. The method of any one of embodiments 1-44, wherein the first plurality of cell-free nucleic acids are analyzed for the copy number aberration based on re-binning, combining windows, or hidden Markov model analysis, or a combination thereof 46. The method of any one of embodiments 1-45, wherein performing the second assay comprises determining a methylation status of the second sample of cell-free nucleic acids. 47. The method of embodiment 46, wherein the methylation status of a subset of the cell-free nucleic acids from the second sample is used to identify a tissue of origin of the subset of the cell-free nucleic acids from the second sample. 48. The method of embodiment 47, wherein the tissue of origin is a liver tissue. 49. The method of any one of embodiments 46-51, wherein the methylation status of a subset of the cell-free nucleic acids from the second sample is used to identify a cancer type from which the subset is derived. 50. The method of embodiment 49, wherein the cancer type is hepatocellular carcinoma. 51. The method of any one of embodiments 46-50, wherein determining the methylation status comprises determining a methylation haplotype. 52. The method of any one of embodiments 1-51, wherein the second assay comprises analyzing a fragment size of a subset of cell free nucleic acids from the second sample. 53. The method of embodiment 52, further comprising using the fragment size to identify a tissue from which the subset of the cell-free nucleic acids from the second sample is derived. 54. The method of embodiment 53, wherein the tissue is a liver tissue. 55. The method of any one of embodiments 52-54, further comprising using the fragment size to identify a cancer type from which the subset of the cell-free nucleic acids from the second sample is derived. 56. The method of embodiment 55, wherein the cancer type is hepatocellular carcinoma. 57. The method of any one of embodiments 52-56, wherein the analyzing the fragment size comprises filtering out sequences above a size threshold. 58. The method of any one of embodiments 1-57, wherein the second assay comprises identifying somatic mutations in the second sample comprising cell-free nucleic acids. 59. The method of embodiment 58, wherein the second assay comprises filtering out sequence reads corresponding to somatic mutations in white blood cells from the subject. 60. The method of any one of embodiments 1-59, wherein the positive predictive value for the condition being present based on the second assay is at least 1.5-fold, 2-fold, 5-fold, 10-fold, 20-fold, 50-fold, or 100-fold greater than the positive predictive value for the condition being present based on the first assay. 61. The method of any one of embodiments 1-59, wherein the positive predictive value for the condition being present based on the first assay and the second assay is at least 1.5-fold, 2-fold, 5-fold, 10-fold, 20-fold, 50-fold, or 100-fold greater than the positive predictive value for the condition being present based on the first assay.

62. A method of screening for a condition of a subject, the method comprising: (a) obtaining a first plurality of cell-free nucleic acids from the subject, wherein at least a subset of the first plurality of cell-free nucleic acids is potentially originated from a liver tissue of the subject; (b) performing a first assay comprising analyzing sequencing data of the first plurality of cell-free nucleic acids for copy number aberrations; (c) performing a second assay comprising analyzing sequencing data of a second plurality of cell-free nucleic acids from the subject, wherein at least a subset of the second plurality of cell-free nucleic acids is potentially originated from a liver tissue of the subject, wherein a positive predictive value for the condition being present based on the first assay and the second assay is greater than a positive predictive value for the condition being present based on the first assay, thereby screening for the condition of the subject.

63. The method of embodiment 62, wherein the condition is a liver condition. 64. The method of embodiment 63, wherein the liver condition is selected from the group consisting of liver cirrhosis, hepatocellular carcinoma, nonalcoholic fatty liver disease, nonalcoholic steatohepatitis, and a combination thereof 65. The method of any one of embodiments 62-64, wherein the first plurality of cell-free nucleic acids and the second plurality of cell free nucleic acids are from one or more biological samples from the subject. 66. The method of embodiment 65, wherein the first plurality of cell-free nucleic acids and the second plurality of cell free nucleic acids are the same. 67. The method of any one of embodiments 62-66, wherein the at least a subset of the first plurality of cell-free nucleic acids and the at least a subset of the second plurality of cell-free nucleic acids comprise cell-free nucleic acids that are from hepatocellular carcinoma. 68. The method of any one of embodiments 62-67, wherein the copy number aberration comprises a duplication or a deletion of a genomic locus. 69. The method of any one of embodiments 62-68, wherein the second assay is used to determine that the subset of the second plurality of cell-free nucleic acids is from the liver tissue. 70. The method of any one of embodiments 62-69, wherein the condition is a cancer type, and wherein the second assay is used to determine the cancer type. 71. The method of embodiment 70, wherein the cancer type is hepatocellular carcinoma. 72. The method of any one of embodiments 62-71, wherein the first plurality of cell-free nucleic acids and the second plurality of cell-free nucleic acids are from one or more plasma samples. 73. The method of any one of embodiments 62-72, wherein the first plurality of cell-free nucleic acids comprises deoxyribonucleic acids or ribonucleic acids. 74. The method of any one of embodiments 62-73, wherein the second plurality of cell-free nucleic acids comprises deoxyribonucleic acids or ribonucleic acids. 75. The method of any one of embodiments 62-74, wherein the sequencing comprises whole genome sequencing or targeted sequencing. 76. The method of embodiment 62, wherein the first assay comprises an amplification of the first plurality of cell-free nucleic acids before the sequencing. 77. The method of embodiment 76, wherein the amplification comprises a whole genome amplification or a targeted amplification. 78. The method of embodiments 62, wherein the first plurality of cell-free nucleic acids are not amplified before the sequencing. 79. The method of any one of embodiments 62-78, wherein the first plurality of cell-free nucleic acids are analyzed for the copy number aberration based on re-binning, combining windows, or hidden Markov model analysis. 80. The method of any one of embodiments 62-79, wherein an average fragment size of the at least a subset of the first plurality of cell-free nucleic acids is smaller than an average fragment size of the other cell-free nucleic acids from the first plurality of cell-free nucleic acids. 81. The method of any one of embodiments 62-80, wherein an average fragment size of the at least a subset of the second plurality of cell-free nucleic acids is smaller than an average fragment size of the other cell-free nucleic acids from the second plurality of cell-free nucleic acids. 82. The method of any one of embodiments 62-81, wherein the second assay comprises determining a methylation status of the second plurality of cell-free nucleic acids. 83. The method of embodiment 82, wherein the methylation status of a subset of the cell-free nucleic acids from the second biological sample is used to identify a tissue origin of the cell-free nucleic acids from the second biological sample. 84. The method of embodiment 83, wherein the tissue origin is liver. 85. The method of any one of embodiments 82-84, wherein the methylation status of a subset of the cell-free nucleic acids from the second biological sample is used to identify a cancer type from which the subset is derived. 86. The method of embodiment 85, wherein the cancer type is hepatocellular carcinoma. 87. The method of any one of embodiments 82-86, wherein the methylation status comprises a methylation haplotype. 88. The method of embodiment 62, wherein the second assay comprises analyzing a fragment size of the second plurality of cell-free nucleic acids. 89. The method of embodiment 88, further comprising using the fragment size to identify a tissue from which the subset of the plurality of cell-free nucleic acids is derived. 90. The method of embodiment 89, wherein the tissue is a liver tissue. 91. The method of any one of embodiments 88-90, further comprising using the fragment size to identify a cancer type from which the subset of the plurality of cell-free nucleic acids is derived. 92. The method of embodiment 91, wherein the cancer type is hepatocellular carcinoma. 93. The method of any one of embodiments 88-92, wherein the analyzing the fragment size comprises filtering out sequences above a size threshold. 94. The method of any one of embodiments 62-93, wherein the positive predictive value for the condition being present based on the first assay and the second assay is at least 1.5-fold, 2-fold, 5-fold, 10-fold, 20-fold, 50-fold, or 100-fold greater than the positive predictive value for the condition being present based on the first assay. 95. The method of any one of embodiments 62-94, wherein the second assay comprises identifying a somatic mutation in the second plurality of cell-free nucleic acids. 96. The method of embodiment 95, wherein the second assay comprises filtering out sequence reads corresponding to the somatic mutation in white blood cells from the subject. 97. The method of any one of embodiments 62-96, wherein the first assay comprises analyzing sequence reads from a reference chromosome. 98. The method of any one of embodiments 62-97, wherein the first assay comprising analyzing sequence reads at a first depth of 10× or less, 5× or less, 4× or less, 3× or less, or 2× or less. 99. The method of embodiment 98, wherein the second assay comprises analyzing sequence reads at a second depth, wherein the second depth is greater than the first depth. 100. The method of embodiment 99, wherein the second depth is greater than 5×, greater than 10×, greater than 10,000×, or greater than 30,000×. 101. The method of any one of embodiments 62-100, wherein the first assay is performed before the second assay.

102. A method of determining a copy number variation for a subject having or suspected of having a condition, the method comprising: (a) obtaining a first plurality of cell-free nucleic acids from the subject; (b) performing a first assay comprising obtaining sequencing data of the first plurality of cell-free nucleic acids at a first read depth to determine a first assay copy number; (c) comparing the first assay copy number to a threshold to indicate the presence of the copy number variation; (d) obtaining a second plurality of cell-free nucleic acids from the subject; (e) performing a second assay comprising obtaining sequencing data of the second plurality of cell-free nucleic acids from the subject at a second read depth greater than the first read depth to determine a second assay copy number; (f) comparing the second assay copy number to the threshold to indicate the presence of the copy number variation, wherein a positive predictive value for the copy number variation being present based on the first assay and the second assay is greater than a positive predictive value for the copy number variation being present based on the first assay.

103. The method of embodiment 102, wherein the copy number variation is a copy number gain or a copy number loss relative to a subject not having the condition. 104. The method of any one of embodiments 102-103, wherein the first read depth is less than 10×. 105. The method of embodiment 102 or 104, wherein the first read depth is selected from the group consisting of: 1×, 1.5×, 2×, 2.5×, 3×, 3.5×, 4×, 4.5×, and 5×. 106. The method of any one of embodiments 102-105, wherein the second read depth is greater than 10×. 107. The method of any one of embodiments 102-106, wherein the threshold is a copy number determined from a plurality of individuals who do not suffer from the condition. 108. The method of any one of embodiments 102-107, wherein the subject comprises the copy number variation when the first assay copy number is above the threshold. 109. The method of any one of embodiments 102-108, wherein the subject comprises the copy number variation when the second assay copy number is above the threshold. 110. The method of any one of embodiments 102-109, wherein the threshold is a distance from the baseline copy number. 111. The method of any one of embodiments 102-110, wherein the second plurality of cell-free nucleic acids comprises cell-free nucleic acids from a targeted region of the genome of the subject. 112. The method of embodiment 111, wherein the targeted region is a region associated with the condition. 113. The method of embodiment 111, wherein the targeted region is a region identified in the first assay as having the copy number variation.

114. A method of screening for a hepatocellular carcinoma in a subject, the method comprising: (a) obtaining a first plurality of cell-free nucleic acids from the subject, wherein at least a subset of the first plurality of cell-free nucleic acids is potentially originated from a liver tissue; (b) performing a first assay to analyze the first plurality of cell-free nucleic acids for a copy number aberration, the first assay comprising sequencing the first plurality of cell-free nucleic acids; (c) performing a second assay, the second assay comprising determining a methylation status of a second plurality of cell-free nucleic acids from the subject, wherein at least a subset of the second plurality of cell-free nucleic acids is potentially originated from the liver tissue; and (d) comparing the methylation status with one or more reference methylation statuses associated with a hepatocellular carcinoma, thereby screening for the hepatocellular carcinoma in the subject.

115. A method of screening for a hepatocellular carcinoma in a subject, the method comprising: (a) obtaining a first plurality of cell-free nucleic acids from the subject, wherein at least a subset of the first plurality of cell-free nucleic acids is potentially from a liver tissue; (b) performing a first assay to analyze the first plurality of cell-free nucleic acids for a copy number aberration, the first assay comprising sequencing the first plurality of cell-free nucleic acids; (c) performing a second assay to analyze a fragment size of a second plurality of cell-free nucleic acids from the subject, wherein at least a subset of the second plurality of cell-free nucleic acids is potentially from a liver cancer; and (d) comparing the fragment size with one or more reference fragment sizes associated with the hepatocellular carcinoma thereby screening for the hepatocellular carcinoma in the subject.

116. A non-transitory computer-readable medium comprising instructions operable, when executed by one or more computer processors of a computer system, to cause the computer system to: obtaining a first plurality of sequencing reads at a first read depth from a first sample comprising cell-free nucleic acids obtained from the subject, analyze a first plurality of sequencing reads obtained at a first read depth from a first sample comprising cell-free nucleic acids obtained from a subject for a copy number aberration; and detect a presence of the copy number aberration in the first plurality of sequencing reads; conditionally analyze a second plurality of sequencing reads at a second read depth from a second sample comprising cell-free nucleic acids obtained from the subject for a biomarker of a condition of the subject, thereby screening the subject for the condition based on detecting the biomarker in the second plurality of sequencing reads, wherein analyzing the second plurality of sequencing reads is conditionally performed upon the detection of the copy number aberration in the first plurality of sequencing reads; wherein the second plurality of sequencing reads comprises a greater read depth than the first plurality of sequencing reads; and wherein a positive predictive value of screening the subject for the condition based on the analyzing the second plurality of sequencing reads is greater than a positive predictive value of screening the subject for the condition based on analyzing the first plurality of sequencing reads alone.

117. A computer-implemented system comprising: a digital processing device comprising: at least one processor, an operating system configured to perform executable instructions, a memory, and a computer program including instructions executable by the digital processing device to create an application comprising: a software module for obtaining a first plurality of sequencing reads at a first read depth from a first sample comprising cell-free nucleic acids obtained from the subject, analyzing a first plurality of sequencing reads obtained at a first read depth from a first sample comprising cell-free nucleic acids obtained from a subject for a copy number aberration; and detecting a presence of the copy number aberration in the first plurality of sequencing reads; and a software module for conditionally analyzing a second plurality of sequencing reads at a second read depth from a second sample comprising cell-free nucleic acids obtained from the subject for a biomarker of a condition of the subject, thereby screening the subject for the condition based on detecting the biomarker in the second plurality of sequencing reads, wherein analyzing the second plurality of sequencing reads is conditionally performed upon the detection of the copy number aberration in the first plurality of sequencing reads; wherein the second plurality of sequencing reads comprises a greater read depth than the first plurality of sequencing reads; and wherein a positive predictive value of screening the subject for the condition based on the analyzing the second plurality of sequencing reads is greater than a positive predictive value of screening the subject for the condition based on analyzing the first plurality of sequencing reads alone.

118. A non-transitory computer-readable medium comprising instructions operable, when executed by one or more computer processors of a computer system, to cause the computer system to: (a) analyze sequencing reads received from sequencing a first plurality of cell-free nucleic acids from a subject for a copy number aberration, wherein at least a subset of the first plurality of cell-free nucleic acids is potentially from a liver tissue of the subject, wherein less than 60 million sequence reads are analyzed; and (b) analyze sequencing reads received from sequencing a second plurality of cell-free nucleic acids from the subject, wherein at least a subset of the second plurality of cell-free nucleic acids is potentially from the liver tissue of the subject; wherein a positive predictive value for a condition being present in the subject based on (a) and (b) is greater than a positive predictive value for the condition being present in the subject based on (a), thereby screening for the condition of the subject.

119. A non-transitory computer-readable medium comprising instructions operable, when executed by one or more computer processors of a computer system, to cause the computer system to: (a) analyze sequencing reads received from sequencing a first plurality of cell-free nucleic acid from a subject for a copy number aberration, wherein at least a subset of the first plurality of cell-free nucleic acids is potentially from a liver tissue from the subject; and (b) analyze sequencing reads received from sequencing a second plurality of cell-free nucleic acids from the subject, the analysis comprising determining a methylation status of the second plurality of cell-free nucleic acids, wherein at least a subset of the second plurality of cell-free nucleic acids is potentially from the liver tissue from the subject; and (c) compare the methylation status with one or more reference methylation statuses associated with hepatocellular carcinoma, thereby screening for hepatocellular carcinoma in the subject.

120. A non-transitory computer-readable medium comprising instructions operable, when executed by one or more computer processors of a computer system, to cause the computer system to: (a) analyze sequencing reads received from sequencing a first plurality of cell-free nucleic acids from a subject for a copy number aberration, wherein at least a subset of the first plurality of cell-free nucleic acids is potentially from a liver tissue from the subject; and (b) analyze sequencing reads received from sequencing a second plurality of cell-free nucleic acids from the subject, the analysis comprising determining a fragment size of the second plurality of cell-free nucleic acids, wherein at least a subset of the second plurality of cell-free nucleic acids is potentially from the liver tissue of the subject; and (c) compare the fragment size with one or more reference fragment sizes associated with hepatocellular carcinoma, thereby screening for hepatocellular carcinoma in the subject.

VII. EXAMPLES

The following examples are included for illustrative purposes only and are not intended to limit the scope of the invention.

Example 1: Increasing the Positive Predictive Value of a Cancer Screening Test Based on Copy Number Aberration Blood is drawn from a patient suspected of having cancer into a collection tube. Cells are removed from plasma containing cell-free DNA (cfDNA) by performing centrifugation 2 times in series. Centrifugation is performed for 10 minutes at 2,000×g to deplete platelets and cells from the plasma sample. cfDNA extraction is performed on the plasma sample to enrich the plasma sample for cfDNA. The cfDNA sample is divided into two different aliquots. A first aliquot of the cfDNA is used in a first assay while a second aliquot of the cfDNA is stored in a freezer for later use in a second assay.

The first aliquot of cfDNA is assays for chromosomal copy number aberration using massively parallel paired-end sequencing. The sequences are aligned to a reference genome that has been divided up into a specified number of chromosomal regions. Each region has a specified length. A computer is used to calculate an amount of the cfDNA fragments that align to each chromosome region. These amounts are compared to reference values for the chromosome regions to determine whether a copy number aberration is present in one or more of the chromosome regions. Increases in the amounts of cfDNA fragments corresponding to a particular region above a threshold relative to the reference values are deemed duplications or amplifications. Decreases in the amounts of cfDNA fragments corresponding to a particular region below a threshold relative to the reference values are deemed deletions. A significant number of copy number aberrations are detected in the first aliquot.

Because the subject's blood level indicates the presence of copy number aberrations above the threshold, a second assay including a methylation analysis of cell-free DNA fragments in the plasma sample is performed. Methylation-sensitive sequencing is first performed to obtain sequence reads corresponding to each end of the cell-free DNA fragments in the sample. The sequence reads are aligned to a reference genome to determine a location of each sequence read, as well as the methylation status at various genomic locations. Sequencing and alignment are performed for each cell-free DNA fragment in the sample to obtain a methylation pattern (e.g., an amount of methylation and/or a methylation status at multiple genomic locations) corresponding to the methylation of the cell-free DNA fragments. The methylation pattern is compared to a reference obtained from the MethHC database to confirm the presence of cancer and determine a tissue of origin from which the cancer-derived cell-free DNA fragments are derived. The tissue of origin is determined to be liver and the patient is suspected of having hepatocellular carcinoma.

The methylation assay is determined to have a much lower false positive rate than the first assay. The combination of the first assay and the second assay increases the positive predictive value of determining if the subject has hepatocellular carcinoma compared to using the first assay alone. This is achieved without compromising the sensitivity of the assay. Furthermore, this increase in positive predictive value is achieved using a single blood sample.

Because the subject's samples are deemed positive for cancer in both screens and the tissue of origin was determined to be liver, a more invasive procedure is performed. The patient undergoes a liver biopsy, which confirms the diagnosis.

Example 2: Increasing the Positive Predictive Value of a Cancer Screening Test Based on cfDNA Fragment Size Blood is drawn from a patient suspected of having cancer into a collection tube. Cells are removed from plasma containing cell-free DNA (cfDNA) by performing centrifugation 2 times in series. Centrifugation is performed for 10 minutes at 2,000×g to deplete platelets and cells from the plasma sample. cfDNA extraction is performed on the plasma sample to enrich the plasma sample for cfDNA. The cfDNA sample is divided into two different aliquots. A first aliquot of the cfDNA is used in a first assay while a second aliquot of the cfDNA is stored in a freezer for later use in a second assay.

The first assay analyzes the size of cfDNA fragments in the sample. The cfDNA is sequenced using paired-end (PE) massively parallel sequencing on a by a HiSeq 2000 (Illumina) using the 50-bp×2 PE format. The 50-bp sequence reads are aligned to the non-repeat-masked human reference genome (Hgl 8) (genome.ucsc.edu), using the Short Oligonucleotide Alignment Program 2 (SOAP2) (soap.genomics.org.cn). The size of each sequenced fragment is inferred from calculating the number of base pairs between the genomic coordinates corresponding to the outermost nucleotides at each end of the aligned paired end reads. The numbers of fragments corresponding to each of a plurality of sizes is measured and a size profile is determined. If the proportion of cell-free DNA fragments below 150 base pairs in length in the subject's sample is determined to be greater than a cutoff value of 10%, then cancer is considered to be detected in the subject. The patient is suspected of having cancer and it is determined that a second assay should be performed on the second aliquot of cfDNA. It is determined that the first assay has a high sensitivity, but also a high false positive rate.

Because the subject's blood level of short cell-free DNA fragments exceeds the threshold value, a second assay including a methylation analysis of cell-free DNA fragments in the plasma sample is performed. Methylation-sensitive sequencing is first performed to obtain sequence reads corresponding to each end of the cell-free DNA fragments in the sample. The sequence reads are aligned to a reference genome to determine a location of each sequence read, as well as the methylation status at various genomic locations. Sequencing and alignment are performed for each cell-free DNA fragment in the sample to obtain a methylation pattern (e.g., an amount of methylation and/or a methylation status at multiple genomic locations) corresponding to the methylation of the cell-free DNA fragments. The methylation pattern is compared to a reference obtained from the MethHC database to confirm the presence of cancer and determine a tissue of origin from which the cancer-derived cell-free DNA fragments are derived. The tissue of origin is determined to be liver and the patient is suspected of having hepatocellular carcinoma.

The methylation assay is determined to have a much lower false positive rate than the first assay. The combination of the first assay and the second assay increases the positive predictive value of testing the sample compared to using the first assay alone. This is achieved without compromising the sensitivity of the assay. Furthermore, this increase in positive predictive value is achieved using a single blood sample.

Because the subject's samples are deemed positive for cancer in both screens and the tissue of origin was determined to be liver, a more invasive procedure is performed. The patient undergoes a liver biopsy, which confirms the diagnosis.

Figure 2:
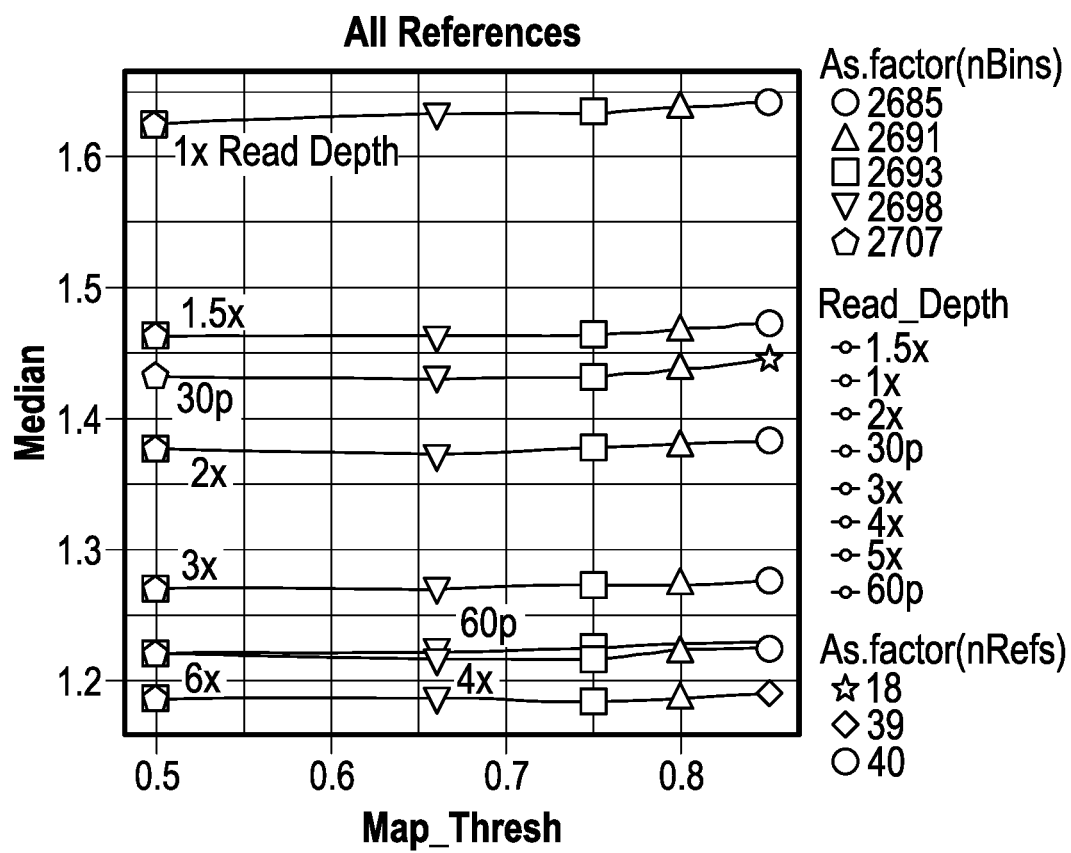
FIG. 2 illustrates median CV versus mappability threshold. The X axis shows the mappability threshold and reads from left to right 0.5, 0.6, 0.7, and 0.8. The Y axis shows the median CV and reads 1.2, 1.3, 1.4, 1.5, and 1.6 from bottom to top.
Figure 3:
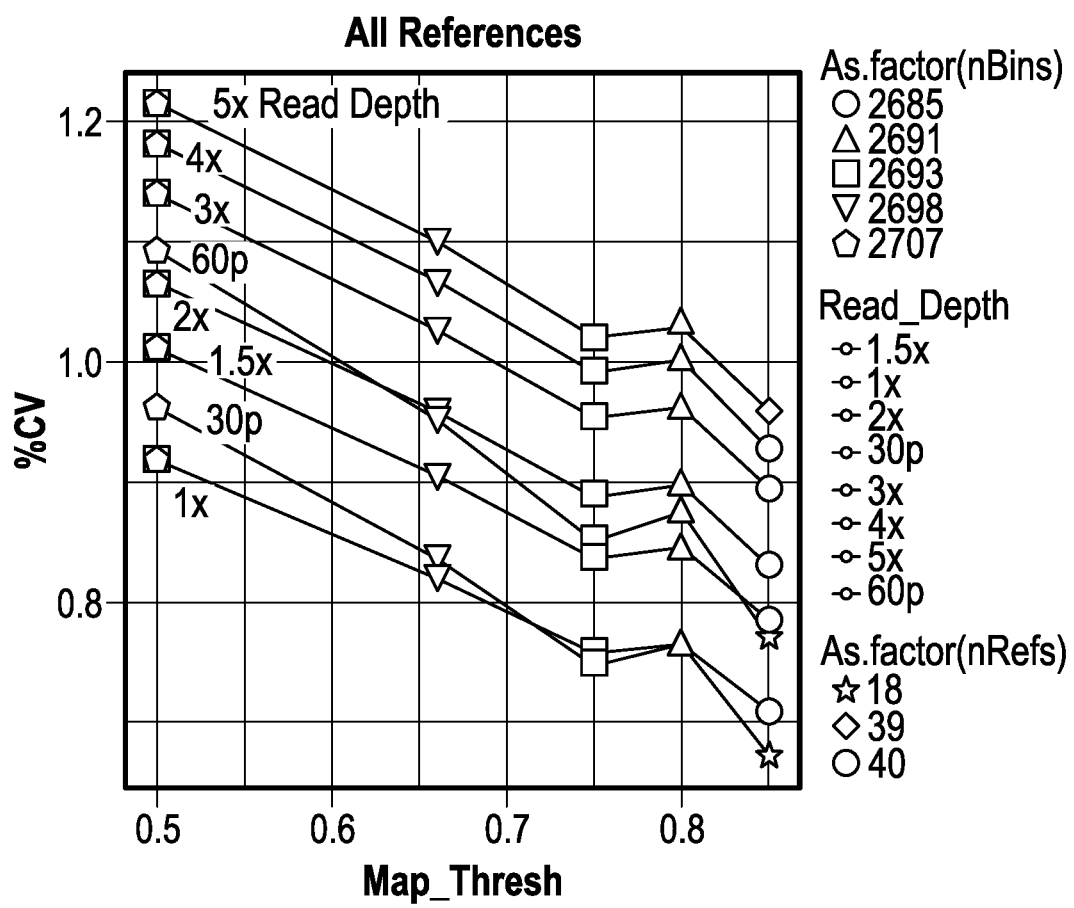
FIG. 3 illustrates mean % CV value versus mappability threshold.

Example 3: Low Depth Whole Genome Sequencing (WGS) to Set Up Baseline in Normal Controls for Detecting Copy Number Signals Whole genome sequencing data (WGS) was obtained from 40 normal individuals with no symptoms of cancer and no detection of pathogens such as HBV. CV (Coefficient of Variance) went down as the sequencing read depth increased (FIG. 1). There was a large decrease in CV value when read depth went from 1× to 1.5× to 2×, while between 4× and 5× the decrease was not as significant. Within each specified depth, the analysis was done at different mappability thresholds to look at median CV (FIG. 2) and percent CV (FIG. 3). Mappability threshold did not seem to have a significant impact.

In conclusion, at 5×, or even 3×, sequence data from normal individuals were sufficient to be used as negative control for subsequent analysis. The data also show that the percent CV decreases as read depth increases.

Example 4: Low Depth Whole Genome Sequencing (WGS) to Detect Copy Number Signals in Pathogenic Individuals Whole genome sequencing data was obtained from several test individuals at two different coverage depths (Table 1). Sequencing data consisted of 2×75 bp paired end reads. Mappability threshold was set at 85%. The read depth of between 1× to 5× was used to look for copy number variation across chromosomes (Table 2).

TABLE 1

Summary of sources of sequencing data.

| Sequencer | Average Coverage | n Normals | n Chronic HBV | n Cirrhosis | n preHCC | n early HCC | n advanced HCC | n Total |
|---|---|---|---|---|---|---|---|---|
| HiSeq2500 | ~2.2× | 30 | 74 | 25 | 23 | 18 | 13 | 183 |
| Next Seq | ~>5× | 47 | 27 | 5 | — | — | 5 | 84 |

Figure 4:
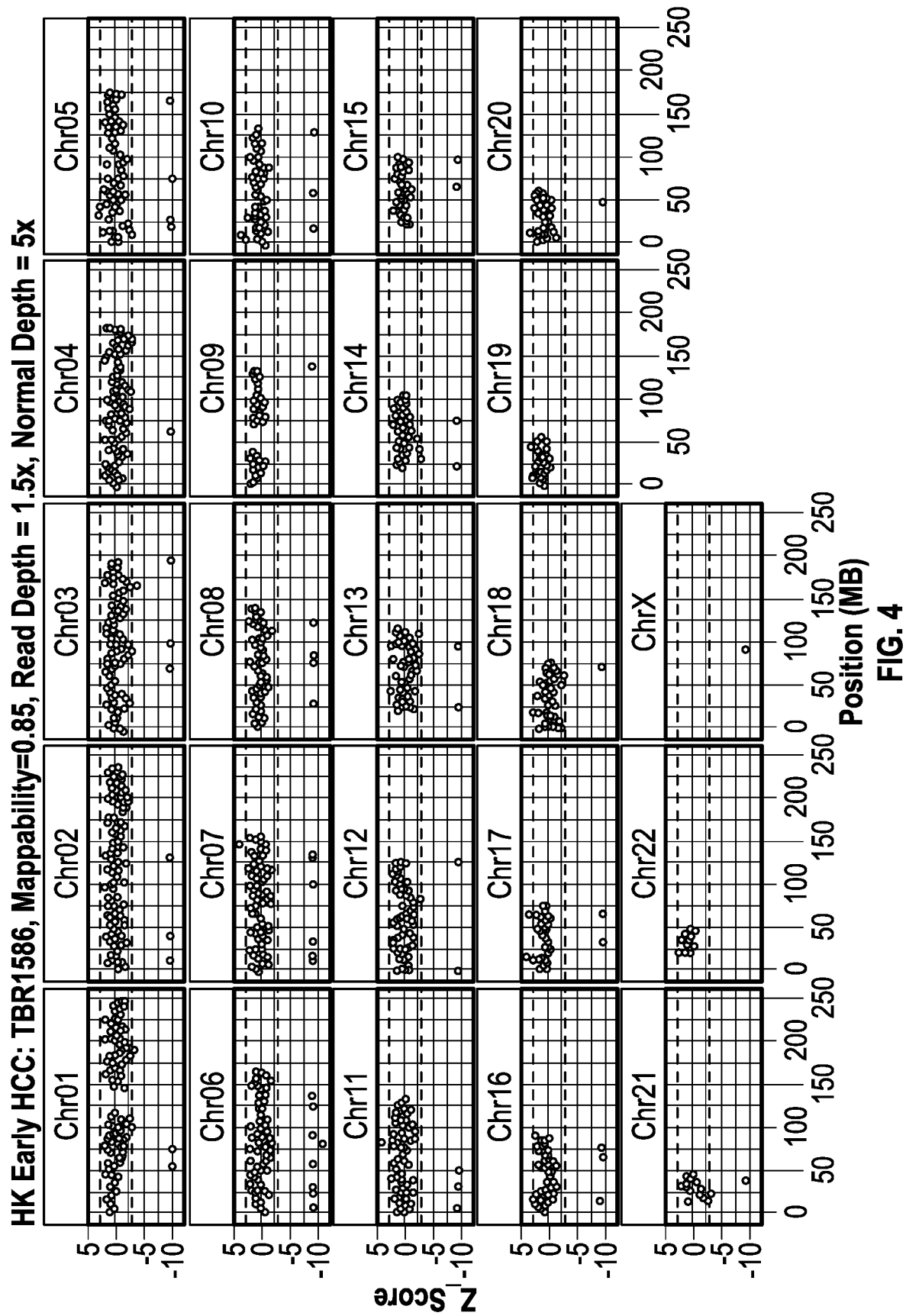
FIG. 4 illustrates sequencing data at 1.5× depth from an early HCC patient. Mappability threshold is 0.85. Each panel is a chromosome from top left (chromosome 1) through bottom right (X chromosome). The X axis in each panel shows the position in megabases and is labeled 0, 50, 100, 150, 200, and 250. The Y axis in each panel shows the Z-score and is labeled −10, −5, 0, and 5 from bottom to top. Grey triangles (upward triangles) denote the locations of CpG clusters correlating with hyper-methylation activities. Black triangles (downward triangles) denote the locations of CpG clusters correlated with hypo-methylation activities.
Figure 5:
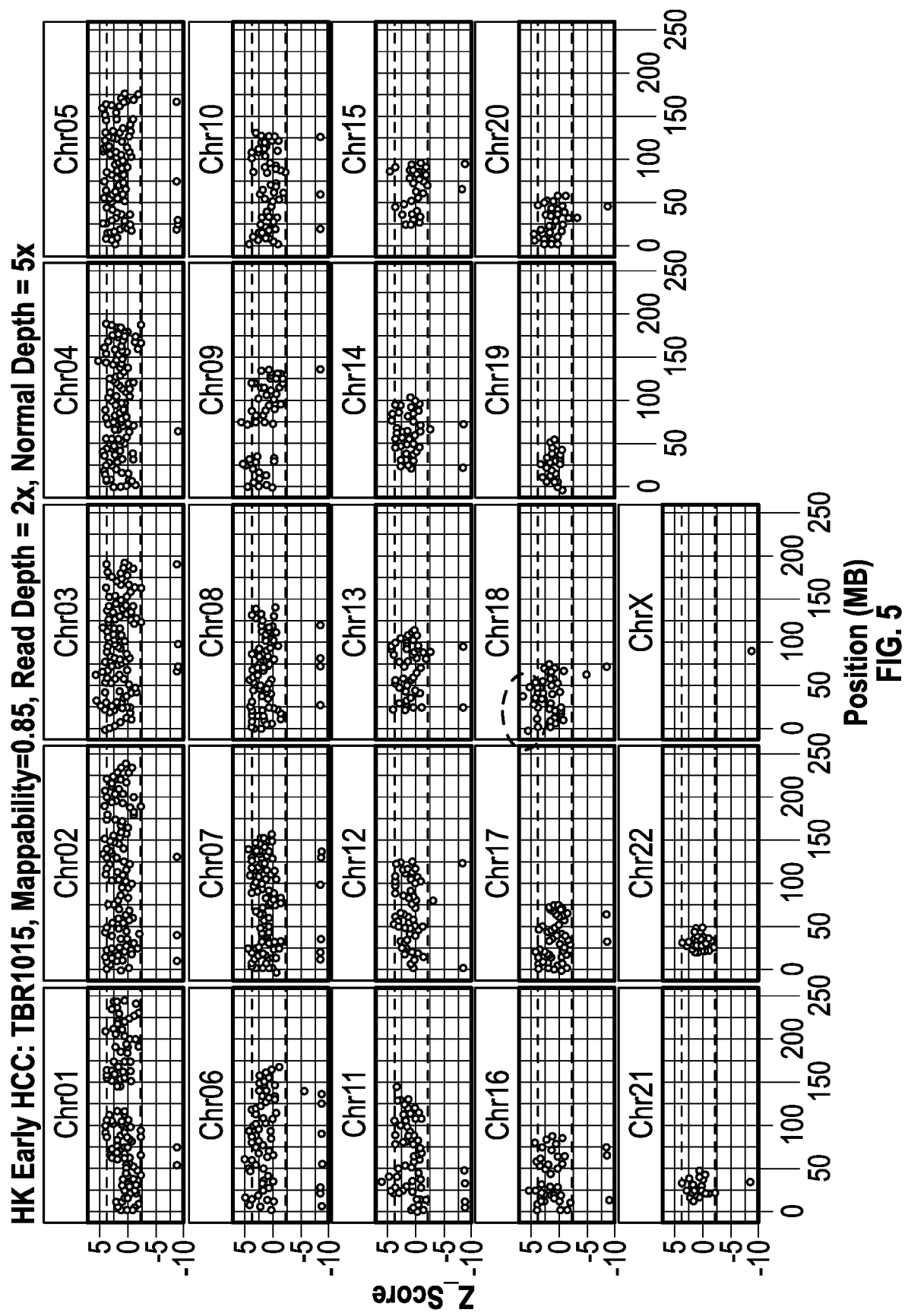
FIG. 5 illustrates sequencing data at 2× depth from an early HCC patient. Mappability threshold is 0.85. Each panel is a chromosome from top left (chromosome 1) through bottom right (X chromosome). The X axis in each panel shows the position in megabases and is labeled 0, 50, 100, 150, 200, and 250. The Y axis in each panel shows the Z-score and is labeled −10, −5, 0, and 5 from bottom to top. Grey triangles (upward triangles) denote the locations of CpG clusters correlating with hyper-methylation activities. Black triangles (downward triangles) denote the locations of CpG clusters correlated with hypo-methylation activities. Circled is an exemplary region of aberrant copy numbers detected.
Figure 6:
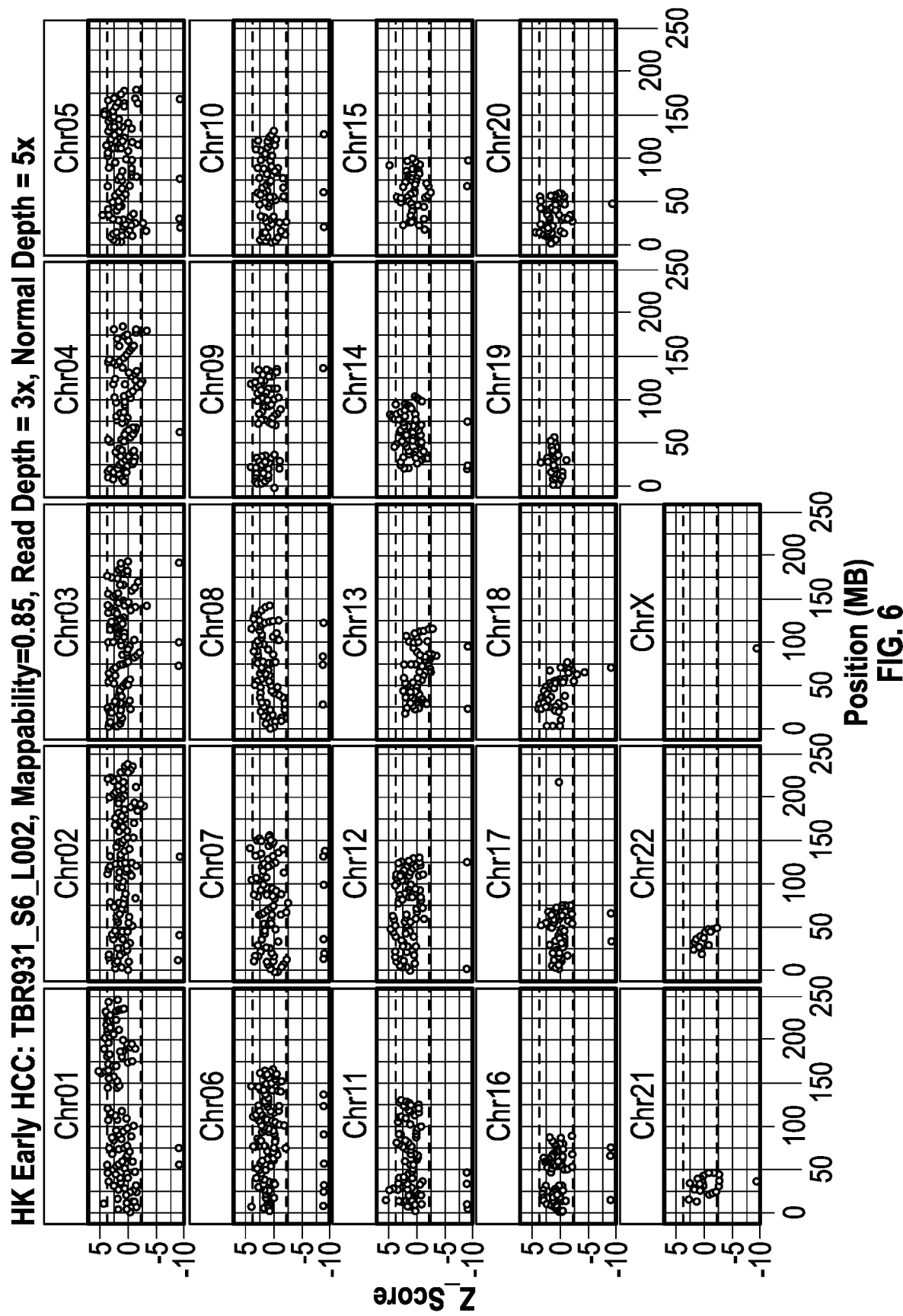
FIG. 6 illustrates sequencing data at 3× depth from an early HCC patient. Mappability is 0.85. Each panel is a chromosome from top left (chromosome 1) through bottom right (X chromosome). The X axis in each panel shows the position in megabases and is labeled 0, 50, 100, 150, 200, and 250. The Y axis in each panel shows the Z-score and is labeled −10, −5, 0, and 5 from bottom to top. Grey triangles (upward triangles) denote the locations of CpG clusters correlating with hyper-methylation activities. Black triangles (downward triangles) denote the locations of CpG clusters correlated with hypo-methylation activities.

Sequencing data with a depth at 1.5× depth from an early HCC patient showed little copy number (FIG. 4), while sequencing depth at 2× (FIG. 5) and 3× (FIG. 6) lead to the identification of some copy number signals in certain regions. For advanced HCC patients, it was possible to identify copy number variants at a depth as low as 1× (Table 2). In particular some copy number variations were identified in chromosome 13 and may relate to immune response associated with early HCC. Additionally, copy number variations were identified in chromosome 18.

Sequencing data was also used to detect liver-related CpG clusters, which were common across all patients sequenced. Combining such known tissue markers with low depth copy number analysis in a first assay is used to identify patients for further screening using a second assay focused on selected chromosomal regions. For example, a targeted assay at a higher sequencing depth or a methylation assay could be used to focus on liver-related regions on chromosome 13 or 18. The combination of using the low depth WGS with the second assay to further screen the patients yields a higher positive predictive value than using the low depth WGS alone.

Patients who tested positive for HBV but who did not have cancerous systems were also tested (Table 2). Possible copy number variation signals were identified in chromosomes 13, 4, 3, 1, 2, 7, etc. Several patients showed copy number variation signals in many chromosomes, but consistency is found in selected regions in, for example, chromosomes 4, 8, and 13.

Some copy number variants were picked up for normal patients, for example in chromosome 13 (Table 2). Three different HMM-based analyses were used to identify and locate copy number changes: The first method included using the circular binary segmentation (CBS) algorithm of Olshen and Seshan (Olshen A. B., et al. Circular binary segmentation for the analysis of array-based DNA copy number data, Biostatistics, 2004, vol. 5 (pg. 557-572)). The CBS algorithm analyzes genomic data by recursively splitting chromosomes into either two or three subsegments based on a maximum t-statistic. The algorithm estimates a reference distribution by permutation, which is used to decide whether or not to split. The algorithm provides options to eliminate splits when the means of adjacent segments are not sufficiently far apart. This method was implemented using the runDNAcopy function available from Bioconductor.org. The second method utilized runHomHMM, which fits an unsupervised Hidden Markov Model to a given dataset. runHomHMM is a function snapCGH v1.42.0, which is freely available. The third method used runBioHMM, which reads in a dataset of log 2 ratios and the corresponding clone and covariate information. It calculates a heterogeneous HMM when there are 1, 2, 3, 4 or 5 underlying states and chooses between them using either the AIC or BIC. It then assigns clones using a modified version of the Viterbi algorithm. runBioHMM is also a function of snapCGH v.1.42.0. This suggested that a low depth whole genome sequencing assay can be used to broadly survey chromosomal regions that may be associated with different cancer types.

TABLE 2

Chromosome locations of copy number signals in patients with Hepatitis B virus (HBV), early or advanced hepatocellular carcinoma (HCC), pre-HCC, or normal patients.

| Patient. No. | Status | Read depth | Chromosomal location(s) of copy number signals detected using all three methods | Chromosomal location(s) of copy number signals detected by 2 different methods |
| --- | --- | --- | --- | --- |
| GM4468 | Chronic HBV | 2× | 13 | |
| GM3137 | Chronic HBV | 5× | 4 | |
| GM4494 | Chronic HBV | 2× | 3, 13, 21 | |
| GM2079 | Chronic HBV | 5× | 1, 2, 3, 4, 11, 13 | 8 |
| GM4218 | Chronic HBV | 3× | 2, 3, 4, 5, 7, 10, 11, 12, 13, 14, 15, 16, 20, 21 | |
| GM2227 | Chronic HBV | 5× | 1, 2, 3, 5, 11, 13, 21 | 3 |
| GM4383 | Chronic HBV | 2.5× | 13 | |
| GM2258 | Chronic HBV | 3× | 13 | |
| GM2525 | Chronic HBV | 5× | 1, 8, 11, 12, 13, 22 | 4 |
| GM2521 | Chronic HBV | 5× | 13 | |
| GM2490 | Chronic HBV | 5× | 1, 2, 3, 4, 11, 13 | |
| GM4755 | Chronic HBV | 3× | 4, 7, 8, 13, 20, 21 | 4 |
| GM4753 | Chronic HBV | 2.5× | 8, 13, 21 | |
| GM4218 | Chronic HBV | 2.5× | 1, 2, 3, 4, 5, 6, 9, 12, 13, 14, 16, 19, 20 | 3, 4, 5, 9, 13, 17, 21 |
| TBR1586 | Early HCC | 1.5× | | |
| TBR1015 | Early HCC | 2× | 18 | |
| TBR931 | Early HCC | 3× | | |
| TBR1385 | Advanced HCC | 2.5× | | 13 |
| TBR1331_S9 | Advanced HCC | 1× | 18 | |
| TBR1331-2 | Advanced HCC | 1.5× | 16, 18 | |
| AB020 | Normal | 2× | 1, 13, 22 | 4 |
| AC030 | Normal | 2.5× | 2, 21 | 8 |
| AB030 | Normal | 1.5× | 1 | 13 |
| CTR245 | Normal | 2× | 13 | |
| AH020 | Normal | 1.5× | 13 | 1 |
| AB040 | Normal | 2× | 3, 4 | |
| GM7742 | Pre-HCC | 1.5× | 2, 4, 19 | |
| GM5330 | Pre-HCC | 2.5× | 8, 9, 20 | |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method of screening for a cancer of a subject, the method comprising:
performing a first assay comprising:
sequencing a first plurality of cell-free nucleic acids at a first read depth to provide a first plurality of sequencing reads at a first read depth, wherein the first plurality of cell-free nucleic acids are from a first sample obtained from the subject, analyzing the first plurality of sequencing reads to determine a first assay copy number of the first sample of cell-free nucleic acids; and comparing the first assay copy number to a threshold to determine a presence or absence of the copy number aberration in the first plurality of sequencing reads; and determining that the first plurality of sequencing reads are indicative of the presence of the copy number aberration, performing a second assay subsequent to the performing of the first assay, the second assay being different from the first assay, the second assay comprising:

performing a targeted methylation-sensitive sequencing on a second plurality of cell-free nucleic acids enriched for a targeted region of the genome of the subject, to provide a second plurality of sequencing reads at a second read depth, wherein the second plurality of cell-free nucleic acids are enriched from a second sample obtained from the subject;

determining methylation status of the second plurality of cell-free nucleic acid; and, comparing the methylation status with one or more reference statuses, thereby screening the subject for the cancer, wherein the second plurality of sequencing reads comprises a greater read depth than the first plurality of sequencing reads, such that a positive predictive value of screening the subject for the cancer based on the first and second assays is configured to be greater than a positive predictive value of screening the subject for the cancer based on the first assay alone.

2. The method of claim 1, wherein the first plurality of sequencing reads comprises sequencing reads from a whole genome survey.

3. The method of claim 1, wherein the read depth of the first plurality of sequencing reads is 10× or less, 5× or less, 4× or less, 3× or less, or 2× or less, and the read depth of the second plurality of sequencing reads is 20× or less, 50× or less, 100× or less, 250× or less, 500× or less, 1,000× or less, 2,500× or less, 5,000× or less, 10,000× or less, 15,000× or less, 20,000× or less, 30,000× or less, 40,000× or less, 50,000× or less, 75,000× or less, 100,000× or less, or 250,000× or less.

4. The method of claim 1, wherein the targeted region of the genome comprises a subset of chromosomes, a single chromosome, a subset of genomic loci, or a single genomic locus.

5. The method of claim 1, wherein the first sample and the second sample are obtained from the subject at the same time.

6. The method of claim 1, wherein the first sample and the second sample are each a subsample of a single blood draw from the subject.

7. The method of claim 1, wherein the at least a subset of the first plurality of cell-free nucleic acids and at least a subset of the second plurality of cell-free nucleic acids comprise cell-free nucleic acids that are from a hepatocellular carcinoma.

8. The method of claim 1, wherein the second assay comprises determining that a subset of the second plurality of cell-free nucleic acids is from a liver tissue.

9. The method of claim 1, wherein the cancer is hepatocellular carcinoma.

10. The method of claim 1, wherein the first plurality of cell-free nucleic acids and the second plurality of cell-free nucleic acids are from one or more plasma samples.

11. The method of claim 1, wherein the targeted region is a region associated with the cancer.

12. The method of claim 1, wherein the targeted region is a region determined in the first assay as having the copy number variation.

13. A non-transitory computer-readable medium comprising instructions operable, when executed by one or more computer processors of a computer system, to cause the computer system to:

sequence a first plurality of cell-free nucleic acids at a first read depth to provide a first plurality of sequencing reads, wherein the first plurality of cell-free nucleic acids are from a first sample obtained from the subject, analyze the first plurality of sequencing reads for a copy number aberration to determine a first assay copy number of the first plurality of cell-free nucleic acids;

compare the first assay copy number to a threshold to determine presence or absence of the copy number aberration in the first plurality of sequencing reads;

determine that the first plurality of sequencing reads are indicative of the presence of the copy number aberration perform a targeted methylation-sensitive sequencing on a second plurality of cell-free nucleic acids enriched for a targeted region of the genome of the subject, at a second read depth to provide a second plurality of sequencing reads, wherein the second plurality of cell-free nucleic acids are enriched from a second sample obtained from the subject;

determine methylation status of the second plurality of cell-free nucleic acid; and compare the methylation status with one or more reference statuses, thereby screening the subject for the cancer, wherein the second plurality of sequencing reads comprises a greater read depth than the first plurality of sequencing reads, such that positive predictive value of screening the subject for the cancer based on the analyzing the first and second pluralities of sequencing reads is configured to be greater than a positive predictive value of screening the subject for the cancer based on analyzing the first plurality of sequencing reads alone.

14. A computer-implemented system comprising: a digital processing device comprising: at least one processor, an operating system configured to perform executable instructions, a memory, and a computer program including instructions executable by the digital processing device to create an application comprising:

a first software module for:

sequencing a first plurality of cell-free nucleic acids at a first read depth to provide a first plurality of sequencing reads at a first read depth, wherein the first plurality of cell-free nucleic acids are from a first sample obtained from the subject, analyzing the first plurality of sequencing reads to determine a first assay copy number of the first sample of cell-free nucleic acids;

comparing the first assay copy number to a threshold to determine a presence or absence of the copy number aberration in the first plurality of sequencing reads; and determining that the first plurality of sequencing reads are indicative of the presence of the copy number aberration;
a second software module for:
performing a targeted methylation-sensitive sequencing on a second plurality of cell-free nucleic acids enriched for a targeted region of the genome of the subject, at a second read depth to provide a second plurality of sequencing reads, wherein the second plurality of cell-free nucleic acids are enriched from a second sample obtained from the subject;
determining methylation status of the second plurality of cell-free nucleic acid; and,
comparing the methylation status with one or more reference statuses, thereby screening the subject for a cancer,
wherein the targeted methylation-sensitive sequencing on the second plurality of cell-free nucleic acids is performed after it is determined that the first plurality of sequencing reads are indicative of the presence of the copy number aberration;
wherein the second plurality of sequencing reads comprises a greater read depth than the first plurality of sequencing reads, such that a positive predictive value of screening the subject for the cancer based on the analyzing the first and second pluralities of sequencing reads is configured to be greater than a positive predictive value of screening the subject for the cancer based on analyzing the first plurality of sequencing reads alone.

* * * * *